(12) United States Patent
Pei et al.

(10) Patent No.: US 8,026,073 B2
(45) Date of Patent: Sep. 27, 2011

(54) SCREENING G PROTEIN-COUPLED RECEPTOR ANTAGONISTS FOR METHODS OF TREATING ALZHEIMER'S DISEASE

(75) Inventors: Gang Pei, Shanghai (CN); Yanxiang Ni, Shanghai (CN); Xiaohui Zhao, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 210 days.

(21) Appl. No.: 12/159,183

(22) PCT Filed: Dec. 26, 2006

(86) PCT No.: PCT/CN2006/003595
§ 371 (c)(1), (2), (4) Date: Aug. 18, 2008

(87) PCT Pub. No.: WO2007/073687
PCT Pub. Date: Jul. 5, 2007

(65) Prior Publication Data
US 2008/0312332 A1    Dec. 18, 2008

(30) Foreign Application Priority Data

Dec. 26, 2005  (CN) .......................... 2005 1 0112005
Nov. 17, 2006  (CN) .......................... 2006 1 0162480

(51) Int. Cl.
*G01N 33/53* (2006.01)
(52) U.S. Cl. ....................................................... 435/7.2
(58) Field of Classification Search .......................... None
See application file for complete search history.

(56) References Cited

U.S. PATENT DOCUMENTS

| 5,385,915 A | 1/1995 | Buxbaum et al. |
| 6,187,756 B1 | 2/2001 | Lee et al. |
| 2006/0026702 A1 | 2/2006 | Rockman et al. |

FOREIGN PATENT DOCUMENTS

| CN | 1281334 A | 1/2001 |
| WO | 99/18794 A1 | 4/1999 |
| WO | 9918794 | 4/1999 |
| WO | 03088924 A2 | 10/2003 |

OTHER PUBLICATIONS

Vickers. A vaccine against Alzheimer's disease: developments to date. Drugs Aging 2002; 19(7):487-94.*
Gagnon et al. Role of clathrin-mediated endocytosis in agonist-induced down-regulation of the beta2-adrenergic receptor. J Biol Chem. Mar. 20, 1998;273(12):6976-81.*
International Search Report issued Mar. 29, 2007, by the Patent Cooperation Treaty (PCT) in International Application No. PCT/CN2006/003595, with English translation. (8 pages).
Gao, Hua, et. al., "Identification of b-Arrestin2 as a G Protein-Coupled Receptor-Stimulated Regulator of NF-k B Pathways"; Molecular Cell, May 2004, vol. 14; pp. 303-317.
Li, Xuejun, et. al., "The second cathedra, Molecule mechanism of neurodegenerative disease", Chin J Neurosci, Nov. 2001, vol. 17, No. 4; pp. 379-384.
Chen, Ziwei, et. al., "Development research on G Protein-Coupled Receptor desensitization and internalization"; Development of Physiological Sciences, 2001, vol. 32, No. 1; pp. 55-58.
Supplementary European Search Report issued Feb. 4, 2010, by the European Patent Office in related European Patent Application No. EP-06840640.4 (9 pages).
Reisberg, Barry, M.D., et al., "Novel Pharmacologic Approaches to the Treatment of Senile Dementia of the Alzheimer's Type (SDAT)"; Psychopharmacology Bulletin, Spring 1983, vol. 19, No. 2 (Apr. 1983); pp. 220-225; XP9128232; ISSN: 0048-5764.
Lee, Robert K. K., et al., "Stimulation of amyloid precursor protein synthesis by adrenergic receptors coupled to cAMP formation"; Proceedings of The National Academy of Sciences of USA, National Academy of Science, Washington, DC, U.S.; vol. 94, No. 10, (May 1, 1997); pp. 5422-5426; XP001122046; ISSN: 0027-8424.
Ni, Yanxiang, et al., "Activation of b2-adrenergic receptor stimulates g-secretase activity and accelerates amyloid plaque formation"; Nature Medicine, Nature Publishing Group, New York, NY; vol. 12, No. 12 (Jan. 1, 2006); pp. 1390-1396; XP009105415; ISSN: 1078-8956.
Khachaturlan, Ara S., Ph.D., "Antihypertensive Medication Use and Incident Alzheimer Disease—The Cache County Study"; Archives of Neurology, vol. 63, No. 5 (May 2006); pp. 686-692; XP002564531; ISSN: 0003-9942.

* cited by examiner

*Primary Examiner* — Daniel E Kolker
*Assistant Examiner* — Gregory S Emch
(74) *Attorney, Agent, or Firm* — Osha • Liang LLP

(57) ABSTRACT

A method for screening a reagent for treating or preventing Alzheimer's disease or related neurological pathology includes the steps of: (a) activating a receptor and determining a first extent of endocytosis of the receptor, wherein the receptor is a G-protein coupled receptor that associates with presenilin-1; (b) activating the receptor under the same conditions as in step (a), in the presence of a candidate reagent, and determining a second extent of endocytosis of the receptor; (c) determining a difference between the first extent of endocytosis and the second extent of endocytosis; and (d) repeating steps (a)-(c), if the difference is less than a threshold. Uses of receptor antagonists for manufacturing medicaments for treating or preventing Alzheimer's disease or related neurological pathology, wherein the receptor antagonists inhibit endocytosis of a G-protein coupled receptor that associates with presenilin-1 during endocytosis.

2 Claims, 20 Drawing Sheets

SCREENING G PROTEIN-COUPLED RECEPTOR ANTAGONISTS FOR METHODS OF TREATING ALZHEIMER'S DISEASE

BACKGROUND OF INVENTION

1. Field of the Invention

The present invention relates generally to prevention or treatment of Alzheimer's disease or related neurological pathologies; particularly, it relates to the use of β-adrenergic or opioid receptor antagonists for treating Alzheimer's diseases.

2. Background Art

Alzheimer's Disease (AD), which is characterized by progressive dementia and personality dysfunction, is the most common neurodegenerative disorder associated with aging. AD affects 5-11% of the population over the accumulation of amyloid plaques in the vicinity of degenerating neurons and reactive astrocytes. D. J. Selkoe, Annu. Rev. Neurosci. 17, 489 (1994).

Amyloid plaque, composed mostly of amyloid β (Aβ), is a hallmark of AD neuropathology, and formation of amyloid plaques is considered a primary cause of AD. In addition, recent studies have revealed that the diffusible oligomeric Aβ may also be neurotoxic and potentially AD-related. Walsh, D. M. et al., "Naturally Secreted Oligomers of Amyloid Beta Protein Potently Inhibit Hippocampal Long-Term Potentiation in vivo," *Nature* 416, 535-9 (2002)

Aβ is generated from β-amyloid precursor protein (APP) via sequential cleavages by β- and γ-secretases. As illustrated in FIG. 1, APP is cleaved by β-secretase to produce a soluble $APP_s$-β fragment and a C99 fragment, the latter is in turn cleaved by γ-secretase to produce the Aβ fragment and a C60 fragment.

The amyloid fragments (Aβ) comprise at least two forms, a 40 amino acid form ($A\beta_{40}$) and a 42 amino acid form ($A\beta_{42}$). The 42 amino acid form ($A\beta_{42}$) is more prone to plague formation and is considered more relevant to AD etiology. γ-Secretase plays a pivotal role in AD because it determines the ratio of the two main Aβ species ($A\beta_{40}$ and $A\beta_{42}$).

As shown in FIG. 2, γ-secretase complex includes at least four essential components: presenilin (PS), nicastrin (NC-STN), APH-1, and PEN-2. Mutations in the putative catalytic component presenilin-1 (PS1) account for most cases of familial AD (FAD), suggesting that γ-secretase may be critically involved in the pathogenesis of AD (at least the pathogenesis of FAD).

Although the correlation between presenilin-1 mutations and FAD provides a clue to genetic cause of AD, FAD accounts for less than 10% of all AD cases. In contrast, most AD cases are sporadic in nature, indicating that factors other than presenilin-1 mutations are more important in the pathogenesis of AD. Therefore, it is important to investigate how other factors or environmental influences contribute to AD pathogenesis.

Previous studies have shown that Aβ production in cell cultures can be reduced by activation of intracellular signaling pathways or membrane receptors such as muscarinic acetylcholine receptors. Recent evidence also shows that Aβ levels and amyloid plaque formation can be influenced by somatostatin or environmental factors.

APP processing is also regulated by neurotransmitters and synaptic activity. For example, activation of neurotransmitter receptors, which are coupled to phosphatidylinositol (PI) hydrolysis or to protein kinase C (PKC) activation, can promote APP metabolism and decrease amyloid formation. (Ulus and Wurtman, J. Pharm. Exp. Ther., 281, 149 (1997)) On the other hand, activation of neurotransmitters coupled to cAMP production can suppresses both constitutive and PKC/PI-stimulated APPs secretion in astroglioma cells and in primary astrocytes. (Lee et al., J. Neurochem., 68, 1830 (1997)) The inhibitory effect of cAMP on APPs secretion may be specific for astrocytic cells because cAMP and PKA activation reportedly stimulate APPs secretion in pheocbromocytoma PC-12 and human embryonic kidney cells. (Xu et al., PNAS USA, 93, 4081 (1996); Marambaud et al., J. Neurochem., 67, 2616 (1996)) In any event, the above results indicate that changes in neurotransmitter levels or second messenger signaling, which may result from neuron degeneration and synapse loss in AD, can disrupt APP processing and lead to accumulation of amyloidogenic or neurotoxic APP fragments.

Furthermore, it has been shown that modulation of β-adrenergic receptors, which leads to elevated cAMP, can increase the synthesis of APP in astrocites. Based on this finding, U.S. Pat. Nos. 6,187,756 and 6,043,224, issued to Lee et al., discloses methods for alleviating neurological disorders stemming from the aberrant expression of APP by using β-adrenergic receptor antagonists that modulate the cAMP levels. In this approach, β-adrenergic receptor antagonists are used to suppress the synthesis of APP, through modulation of cAMP levels.

In addition to suppression of APP synthesis, modulation of APP metabolism may also be used to alleviate neurological disorders associated with APP-related plaque formation. For example, U.S. Pat. No. 5,385,915, issued to Buxbaum et al., discloses methods and compositions for affecting APP processing using agents that regulate protein phosphorylation, i.e., agents that affect kinases or phosphatases. The modulation of APP processing in turn leads to the regulation of the production of Aβ peptides that accumulates in amyloidogenic plaques.

Similarly, in U.S. Pat. No. 5,242,932, Gandy et al. disclose and claim a method of modulating or affecting the intracellular trafficking and processing of proteins (including APP) in mammalian cells, using chemicals such as chloroquine and primaquine.

While these prior art methods seem to be effective in modulating the production and metabolism of APP, and hence the formation of plaques, there remains a need for more methods and reagents for the treatment and prevention of AD.

SUMMARY OF INVENTION

Objectives of the present invention include providing methods for screening reagents for treating or preventing Alzheimer's disease or related neurological pathology, thereby providing reagents for treating or preventing Alzheimer's disease or related neurological pathology.

In one aspect, embodiments of the invention relate to methods for screening a reagent for treating or preventing Alzheimer's disease or related neurological pathology. A method in accordance with one embodiment of the invention includes the steps of: (a) activating a receptor and determining a first extent of endocytosis of the receptor, wherein the receptor is a G-protein coupled receptor that associates with presenilin-1; (b) activating the receptor under the same conditions as in step (a), in the presence of a candidate reagent, and determining a second extent of endocytosis of the receptor; (c) determining a difference between the first extent of endocytosis and the second extent of endocytosis; and (d) repeating steps (a)-(c), if the difference is less than a threshold.

Another aspect of the invention relates to methods for screening a reagent for treating or preventing Alzheimer's disease or related neurological pathology. A method in accordance with one embodiment of the invention includes the steps of: (a) measuring a first extent of association between a receptor and presinilin-1 or γ-secretase, wherein the receptor is a G-protein coupled receptor that associates with presenilin-1; (b) measuring a second extent of association between the receptor and presenilin-1 or γ-secretase, under the same conditions as in step (a), in the presence of a candidate reagent; (c) determining a difference between the first extent of association and the second extent of association; and (d) repeating steps (a)-(c), if the difference is less than a threshold.

Another aspect of the invention relates to uses of receptor antagonists for manufacturing medicaments for treating or preventing Alzheimer's disease or related neurological pathology. A use in accordance with one embodiment of the invention is characterized in that the receptor antagonist inhibits endocytosis of a G-protein coupled receptor that associates with presenilin-1 during endocytosis.

Other aspects and advantages of the invention will become apparent from the following description and attached claims.

BRIEF SUMMARY OF DRAWINGS

FIGS. 14a-14e show enhanced γ-secretase activity and Aβ production and accelerated amyloid plaque formation in vivo, while FIGS. 14f and 14g show that a selective β2-adrenergic receptor antagonist, ICI 118,551, was effective in suppressing the formation of β-amyloid plaques. (a and b) Rats were acutely injected with 2 μg norepinephrine (i.c.v.) or 0.5 mg/kg clenbuterol (i.p.). Hippocampi were subjected to fluorogenic substrate assay (a) or rat Aβ ELISA (b), respectively (*P<0.01). (c and d) Representative amyloid plaque burdens in cortex of female (left) and male (right) APPswe/PS1ΔE9 mice after chronic administration of drugs for 30 days. (c) The mice were i.c.v. administered daily with saline or 3 nM Iso. (d) The mice were orally administered daily with saline or 2 mg/kg Cle. Scale bar, 320 μm. (e) Quantitative analysis of areas of amyloid plaque burdens in mice from (c) and (d) (ANOVA, p<0.05). NE, norepinephrine; Sal, saline; Cle, clenbuterol. Enhanced γ-secretase activity and Aβ production, and accelerated amyloid plaque formation in vivo. (a,b) Acute treatment of rats with norepinephrine (NE) or clenbuterol (Cle) enhanced γ-secretase activity (a) and increased secreted Aβ 40 and Aβ 42 levels (b) in hippocampus. *P<0.01. (cg) Cerebral amyloid plaque formation of APPswe/PS1☐E9 mice chronically administered of isoproterenol (c), clenbuterol (d) or ICI 118,551 (ICI) (f). Images in c,d and f: representative plaques in female (left) and male (right) mice. In e: quantitative analysis of amyloid plaque areas in mice from c and d (*P<0.05). In g: same for mice in f (*P<0.05).

FIG. 23A: Representative example of mixed emission spectra of GFP-DOR donor and PS1-Cy3 acceptor fluorophores (excitation, 488-nm laser) are taken before (red line) and after (blue line) photo-bleaching (with 561-nm laser) in HEK293 cells co-transfected with GFP-DOR and HA-ps1. Spectra are shown for one photobleached region (left plot) and another region without photobleaching (right plot) in the same cell. GFP donor emission increases only in the photobleached region of the cell. FIG. 23B: A set of unmixed GFP-DOR and PS1-Cy3 images of 293 cells are taken before and after acceptor photobleaching. The region of photobleaching is indicated by the white outlined box. The enlarged pseudocolored images at the bottom show the intensity of GFP emission in the photobleached and non-photobleached regions of cell surface taken before and after bleaching. The surface-associated intensity of donor GFP-DOR emission in 293 cells increases after acceptor ps1-Cy3 photobleaching. Scale bar indicates 10 μm. FIG. 23C: Averaged FRET efficiencies (%) between surface-associated GFP-DOR and PS1-Cy3. The numbers in the upper the columns indicate the cells taken for experiments. Data are from three independent experiments. **, p<0.01 as compared with the negative control cells transfected with GFP-DOR.

DETAILED DESCRIPTION

The present invention relates to methods for screening reagents for treating or preventing Alzheimer's disease or other related neurological pathologies.

Embodiments of the invention relates to treatments of Alzheimer's disease using antagonists of adrenergic or opioid receptors, particularly β-adrenergic or δ-opioid receptor antagonists. Some embodiments of the invention relate to new uses of β-adrenergic receptor blockers (antagonists) in the treatment of AD, and some embodiments of the invention relate to novel use of δ-opioid receptor (DOR) antagonists for treating Alzheimer's disease. Some embodiments of the invention relate to methods for screening reagents that can be used to treat AD or related neurological pathologies.

As noted above, FAD accounts for about 10% of all AD. Therefore, factors other than genetics may play important roles in AD etiology. Environmental factors, such as stress, may exert their effects by activating receptors, including β-adrenergic receptors (β-ARs) and δ-opioid receptor (DOR), which are G protein coupled receptors (GPCR). Several GPCRs are expressed in the central nervous systems (CNS), especially $β_2$-adrenergic receptor ($β_2$AR), are expressed in hippocampus and cortex, the main regions in the brain involved in AD pathogenesis. In the CNS, these receptors function to mediate signal transduction for epinephrine, dopamines, and opioid peptides, leading to modulation of various neural functions, such as stimulus responses, learning, memory, and pain sensation.

Once activated, these receptors couple to heterotrimeric guanine nucleotide-binding proteins (G proteins) and induce downstream signaling by modulating the levels of intracellular second messengers, such as cAMP. In addition, the activated receptors also undergo clathrin-mediated endocytosis, which plays a crucial role not only in receptor desensitization, but also in signal transduction. The endocytosed GPCR cycles through early endosomes, late endosomes and lysosomes (LEL). The transportation of various endocytic vesicles (endosomes) is mediated by Rab GTPase, which may also serve as a marker for various endosomes.

Embodiments of the invention are based on unexpected findings by the inventors that activation of β-adrenergic receptors (particularly, $β_2$-adrenergic receptors) or δ-opioid receptors can lead to enhanced γ-secretase in the late endosomes and lysosomes (LEL). Being an aspartic protease having an acidic optimal pH, the activity of γ-secretase accumulated in the LEL, which has an acidic environment, is enhanced, leading to increased production of Aβ.

Figure 3:
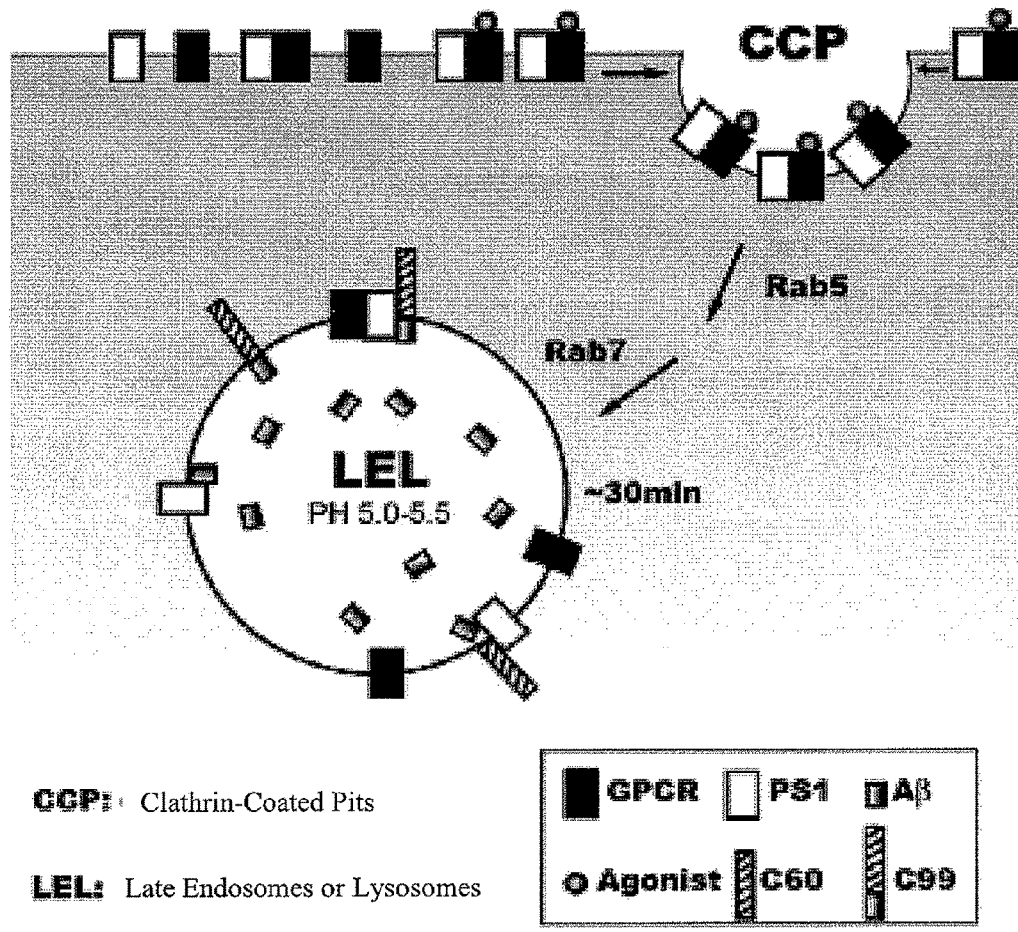
FIG. 3 illustrates a process of endocytosis as a result of receptor activation and trafficking of the endocytosed vesicles to LEL.

FIG. 3 illustrates the path from β-adrenergic receptor or δ-opioid receptor activation to increased production of Aβ. As shown in FIG. 3, activation of β-adrenergic receptors and δ-opioid receptors is accompanied by clathrin-mediated endocytosis, which involves the formation of clathrin-coated pits (shown as CCP in FIG. 3) and pinching off of the CCP. Inventors of the present invention have found that the active-site component of γ-secretase, presenilin-1 (shown as PS1 in FIG. 3), is constitutively associated with these receptors. As a result of such endocytosis, presenilin-1 or γ-secretase is brought into endosomes. Then, through vesicle trafficking mediated by Rab5 and Rab7, these endosomes are transferred to the late endosomes and lysosomes (LEL), where the activities of γ-secretase are enhanced. The enhanced activity of γ-secretase then leads to increased production of Aβ.

These findings suggest that inhibition of β-adrenergic receptors and δ-opioid receptors by antagonists can prevent the enhanced γ-secretase activity. Accordingly, antagonists of these receptors may be used to reduce the production of Aβ, and hence they may be used to prevent or treat AD or related neurological pathologies. As used herein, "antagonist" is used in a broad sense to include compounds that can prevent, reduce, or abolish receptor activation. Such compounds may compete with the receptor agonists for the same binding site, or they may bind to a different site to reduce the effects of agonists.

In addition, these findings suggest that potential antagonists for use in treating or preventing AD or related neurological pathologies may be screened for by monitoring endocytosis of relevant receptors. The endocytosis of these receptors may be determined by monitoring the endocytosis of presenilin-1 (PS1) or γ-secretase, accumulation of presenilin-1 or γ-secretase in LEL, enhanced activity of γ-secretase, or enhanced amyloid-β (Aβ) production.

Figure 4:
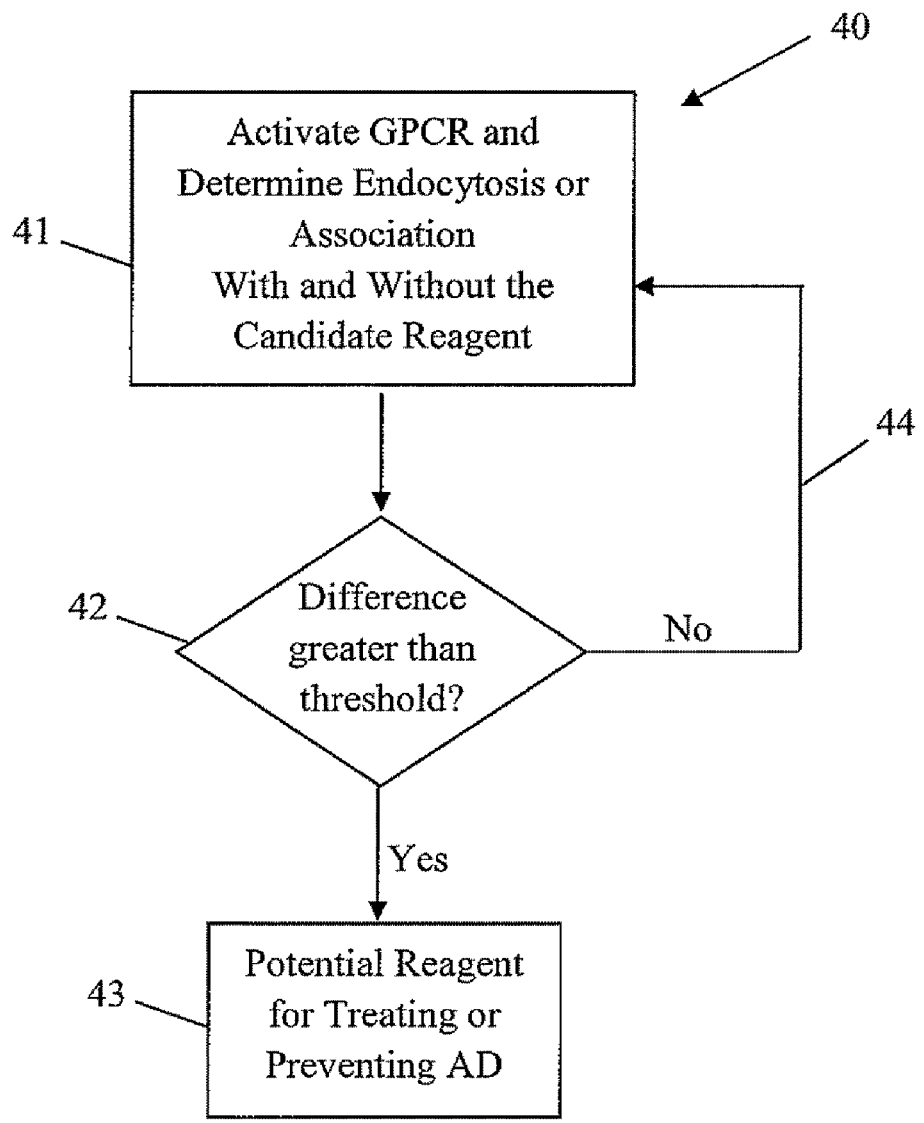
FIG. 4 shows a flow chart of one method in accordance with one embodiment of the invention for screening a receptor antagonist for the treatment or prevention of Alzheimer's disease.

Accordingly, some embodiments of the invention relate to methods for screening reagents that can be used to treat or prevent AD or related neurological pathologies. The screening methods may be based on the abilities of candidate reagents to inhibit endocytosis of receptors that are associated with presenilin-1 or γ-secretase or based on their abilities to reduce or disrupt the association between the receptors and presenilin-1 or γ-secretase. As shown in FIG. 4, a method 40 in accordance with embodiments of the invention includes measuring the extents of endocytosis of a receptor that is associated with presenilin-1 (or γ-secretase) or measuring the extent of association between the receptor and presenilin-1 or γ-secretase, in the presence and absence of a candidate reagent (step 41). Such receptors include G protein-coupled receptors that may be endogenous or from transfection with vectors containing genes encoding the receptors.

Then, the difference in the extents of endocytosis or association in the presence and absence of the candidate reagent is determined (step 42). As noted above, the extent of endocytosis may be monitored by quantifying the endocytosed vesicles, endocytosed presenilin-1 or γ-secretase, accumulation of presenilin-1 or γ-secretase in LEL, enhanced γ-secretase activity in LEL, or enhanced production of Aβ. The extent of association between the receptor and presenilin-1 or g-secretase may be measured using any suitable methods, such as fluorescence energy transfer (FRET) that will be described in detail later.

If the difference in endocytosis or association (as determined in step 42) is significant or exceeds a threshold value, then the candidate reagent can potentially be used to treat or prevent AD or related neurological pathologies (shown as 43). If the difference is insignificant, then the previous step may be repeated with another candidate reagent (shown as 44). Note that while the method in FIG. 4 is illustrated in a sequential manner, in which one candidate reagent is tested at a time, one skilled in the art would appreciate that many reagents may also be simultaneously tested, for example by using a multi-well plate or other large scale or high throughput screening setup.

Some embodiments of the invention relate to methods for treating or preventing Alzheimer's disease or related neurological pathologies by administering to a subject an effective amount of an antagonist that binds β-adrenergic receptor (in particular, β2-adrenergic receptor) and/or δ-opioid receptor. The effective amount of the antagonist is sufficient to reduce receptor endocytosis that starts the process of bringing γ-secretase to the late endosomes and lysosomes (LEL). Other embodiments of the invention relate to the use of an antagonist that binds β-adrenergic receptor (in particular, β2-adrenergic receptor) and/or δ-opioid receptor in the manufacturing of a medicament for treating or preventing Alzheimer's disease or related neurological pathologies.

An effective amount of an antagonist that binds β-adrenergic and/or δ-opioid receptors will depend on the mode of administration, frequency of administration, and the type of pharmaceutical composition used to deliver the compound into a patient, as well as weight, gender, age, and physical conditions of the patient. Typically, an effective dose may range from about 1 μg/Kg body weight to about 10 mg/Kg body weight per day. While individual needs vary, determination of optimal range of effective amounts of each compound is within the skills of one skilled in the art. Administering a compound of the invention to a patient may be via any suitable route used for administering similar pharmaceuticals to a patient, including oral administration, injection, and transdermal patch, to name a few.

Compounds or compositions in accordance with embodiments of the invention may be used to treat Alzheimer's disease or related neurological pathologies in a mammal (human and non-human mammals). Such compounds or compositions of the invention may include pharmaceutically acceptable carriers and/or excipients, such as saline, buffer, glucose, glycerin, alcohol, starch, etc. In addition, these compounds or compositions may be prepared in dosage forms that are commonly used for similar pharmaceuticals, including injections, pills, capsules, patches, etc. Methods for making these dosage forms are well known in the art.

Although various approaches to reducing the production of Aβ have been reported, including modulation of APP production (e.g., U.S. Pat. Nos. 6,187,756 and 6,043,224) and inhibiting APP processing (e.g., U.S. Pat. No. 5,242,932), embodiments of the invention are based on a different mechanism—inhibition of receptor endocytosis that brings γ-secretase to the LEL. The following experiments and examples clearly establish the rationale for using β-adrenergic receptor (particularly, β2-adrenergic receptor) and/or δ-opioid receptor antagonists, or inhibitors to treat or prevent Alzheimer's disease or related neurological pathologies, in accordance with embodiments of the invention.

Example 1

Amyloid β Production is Increased by Activating $\beta_2AR$

Figure 5:
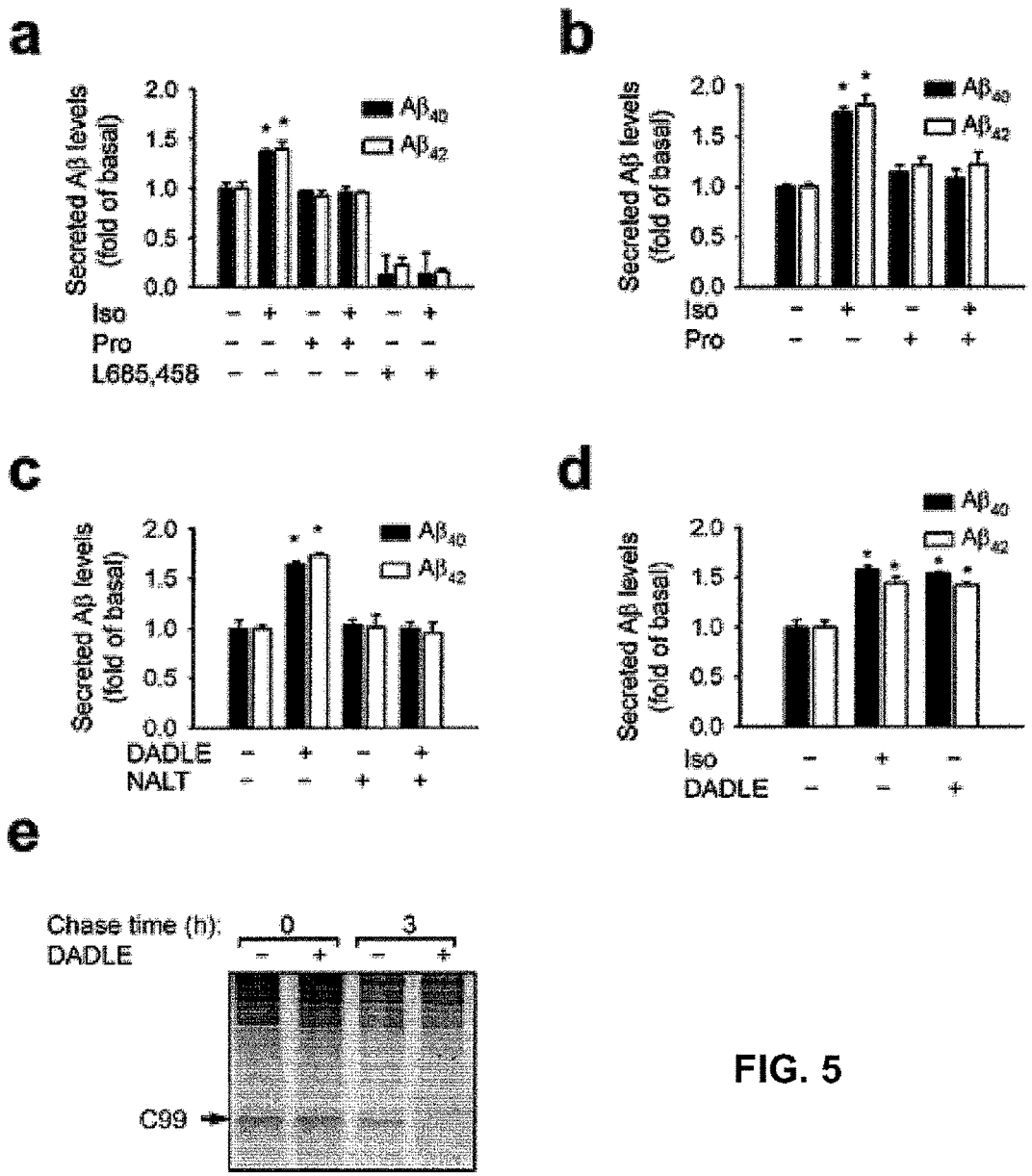
FIGS. 5a-5e show GPCR stimulation increases Aβ production in cell lines and primary hippocampal cells. HEK293 cells co-expressing $β_2AR$ and APPswe (a) were treated for 1 h with 10 μM Iso in the absence or presence of 10 μM Pro after 6-h pre-treatment of vehicle or 1 μM L685,458; HEK293 cells co-expressing $β_2AR$ and C99 (b to c) were treated for 1 h with 10 μM Iso in the absence or presence of 10 μM Pro. Primary hippocampal cultures expressing C99 (d) were treated for 1 h with 10 μM Iso or 1 μM DADLE. Secreted $Aβ_{40}$ (dark bars) and $Aβ_{42}$ (light bars) were detected by ELISA, and their values are the mean±S.E. of three independent experiments and presented as fold values of the basal levels (*P<0.01). (e) Pulse-chase analysis of C99 cleavage in DOR and C99 co-transfected HEK293 cells with or without 1-h treatment of 1 μM DADLE. The data are representative of at least three independent experiments. Con, control; Iso, isoproterenol; Pro, propranolol; DADLE, [D-Ala$^2$, D-Leu5]-Enkephalin. Pro, propranolol; DADLE, [D-Ala$^2$, D-Leu$^5$]-enkephalin; NALT, naltrindole.

The effects of $\beta_2AR$ activation on Aβ production are first assessed in HEK293 cells, which possess functional GPCR signaling pathways and display normal Aβ secretion. The HEK293 cells used in this experiment were transfected with $\beta_2AR$ and mutant APP (APPswe), which harbors FAD-linked "Swedish" mutations at codons 670 and 671. As shown in FIG. 5a, stimulation of $\beta_2AR$ with an agonist, isopranolol (Iso), increased the levels of two secreted Aβ species ($A\beta_{40}$ and $A\beta_{42}$). On the other hand, addition of a $\beta_2AR$ antagonist, propranolol (Pro), which has no effect on its own, abolished the ability of Iso to increase the secreted Aβ levels. The increased Aβ production requires γ-secretase, as evidenced by the fact that pre-treatment with a specific γ-secretase inhibitor L685,458 abolished the increased production of the secreted Aβ.

Figure 1:
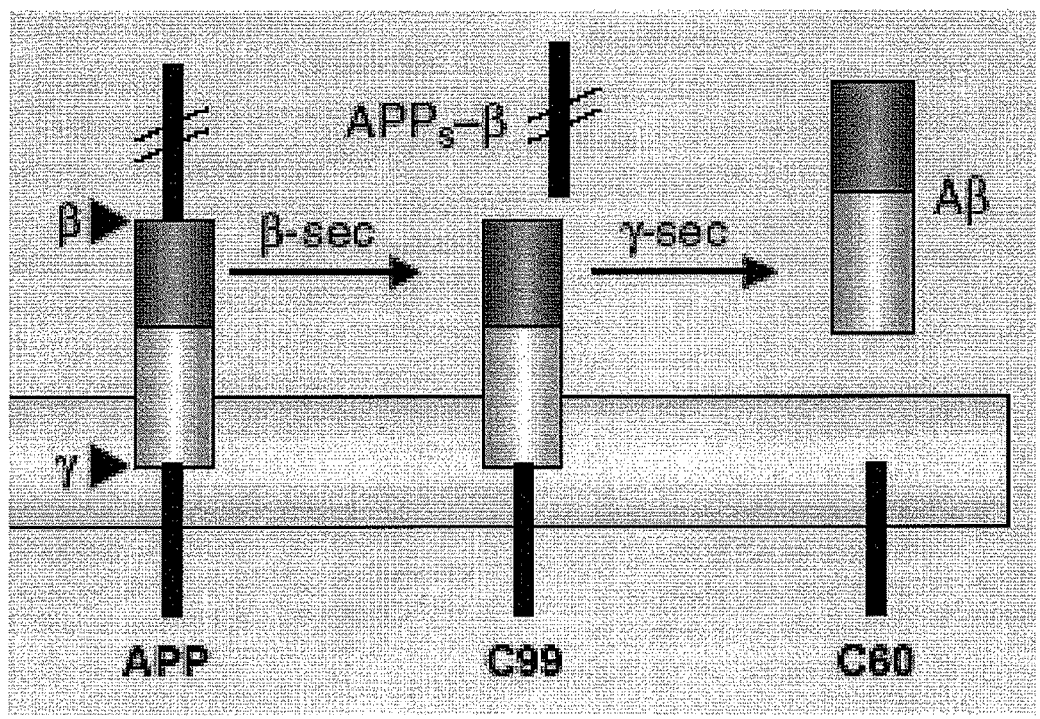
FIG. 1 illustrates the process of sequential actions of β-secretase and γ-secretase in the formation of Aβ from APP. APP is first cleaved by β-secretase to generate a soluble APPs-β and C99. C99 is in turn cleaved by γ-secretase to generate Aβ and C60.
Figure 2:
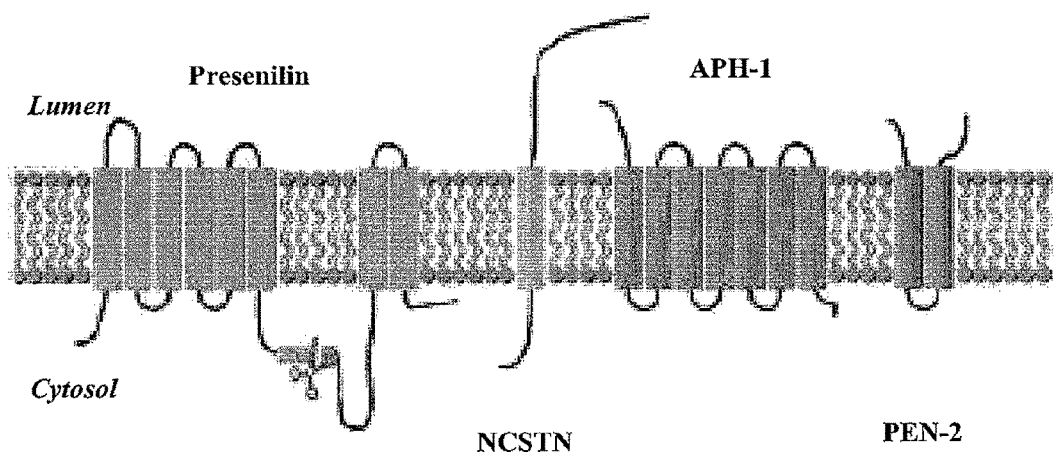
FIG. 2 shows the four main components of γ-secretase: presenilin, nicastrin (NCSTN), ACH-1, and PEN-2.

The fact that γ-secretase is involved in the $\beta_2AR$-induced production of Aβ is further corroborate by co-transfection of a γ-secretase substrate (C99) and $\beta_2AR$ into HEK293 cells. C99 is a product of O-secretase-mediated cleavage of APP (see FIG. 1). C99 functions as a direct substrate of γ-secretase as well as an immediate precursor to $A\beta^{26}$. FIG. 5b shows that stimulation of $\beta_2AR$ with Iso resulted in an increase in Aβ production in the co-transfected HEK293 cells, similar to the above-described results using cells co-transfected with APPswe and $\beta_2AR$. This increase was again abolished by the presence of Pro, which had no effect per se. Thus, the increase in the secreted Aβ was likely due to an enhanced γ-secretase activity.

In addition to $\beta_2AR$, activation of δ-opioid receptor (DOR) was also found to result in increases in secreted Aβ levels. As shown in FIG. 5c, DADLE (D-Ala$_2$-D-Leu$_5$-enkephalin, an agonist of δ-opioid receptor) treatment in C99-transfected HEK293 cells resulted in increased production of Aβ. Treatment with a δ-opioid receptor antagonist, NALT (δ-naltrindole), abolished the effect of DADLE. While the above experiments used cells having transfected receptors, the same results were seen with endogenous receptors. FIG. 5d shows that in primary hippocampal culture cells transfected with C99, stimulation of endogenous β-ARs or DOR also led to an elevation of secreted Aβ.

The above results clearly indicates that activation of β-AR or DOR leads to increased secretion of Aβ. The production of the secreted Aβ is from cleavage of the transfected C99 substrate as shown in a pulse-chase experiment. As shown in FIG. 5e, the turnover of C99 in the HEK293 cells co-transfected with DOR and C99 was more rapid in the presence of DADLE (a DOR agonist) treatment than in the absence of DADLE treatment. This result suggests that the C99 cleavage was facilitated by receptor activation. Thus, activation of β-adrenergic receptors (β-AR) (particularly, $\beta_2AR$) and/or DOR enhances the production and secretion of Aβ as a result of promoted cleavage of C99 (or similar substrates) by γ-secretase.

Example 2

Activation of $\beta_2AR$ Enhances γ-Secretase Activity

The enhanced production of Aβ upon activation of β-AR or DOR described above could result from increased γ-secretase expression or enhanced γ-secretase activity. To answer this question, the effect of $\beta_2AR$ activation on γ-secretase expression and activation was assessed. As shown by Western blot analysis in FIG. 6a, C60, the produced from γ-secretase-mediated cleavage of C99, production was increased after Iso treatment of the C99-transfected HEK293 cells. However, the same treatment failed to produce any change in the expression level of PS1, which is the active site component of γ-secretase and exists as a heterodimer of an amino- and a carboxyl-terminal fragments (PS1-NTF and PS1-CTF). This result suggests that $\beta_2AR$ activation increased γ-secretase activity, without changing the γ-secretase expression.

Figure 6:
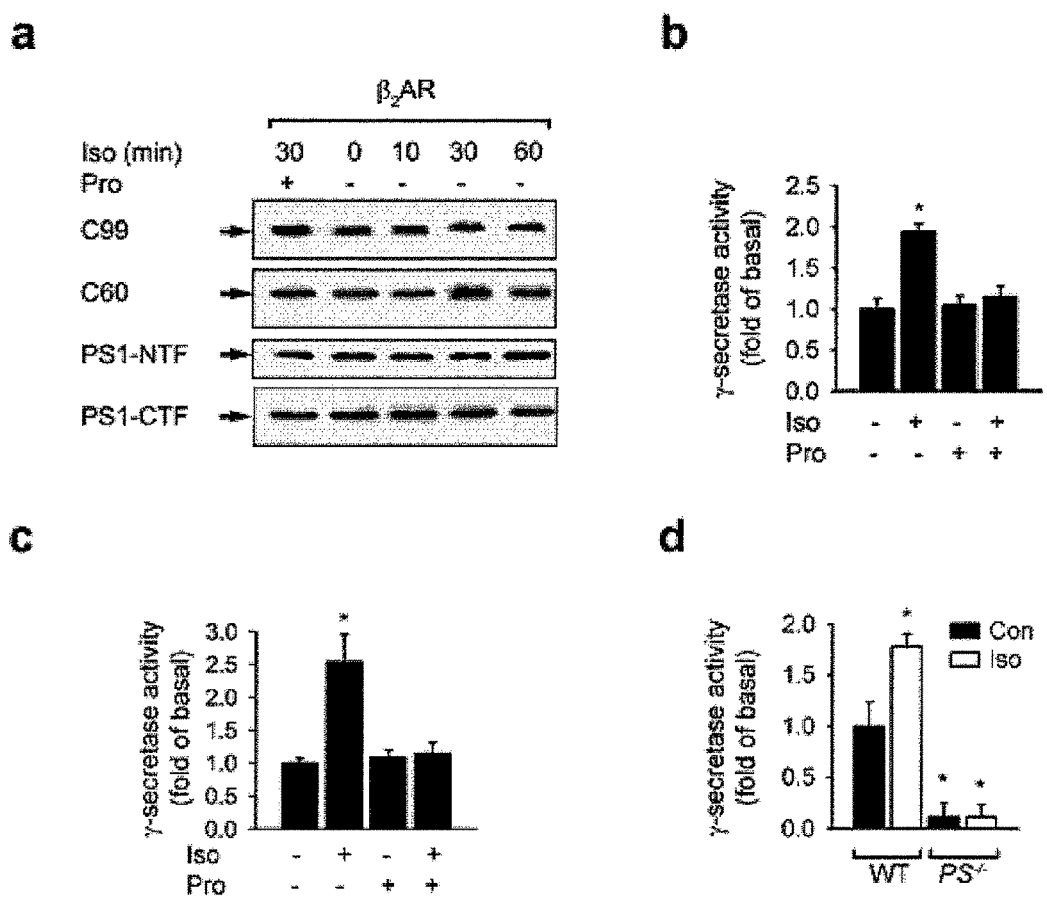
FIGS. 6a-6d show $β_2AR$ stimulation enhances γ-secretase activity in neuronal cells. (a) HEK293 cells co-transfected with C99 and $β_2AR$ were treated for different time with 10 μM Iso in the absence or presence of 10 μM Pro. The cell membrane fractions were incubated in vitro at 37° C. for 2 h and the generated C60 from these cell membrane fractions were detected by Western blot. The data are representative of at least four independent experiments. (b to d) C6 glioma (b), rat acute hippocampal slices (c), and $β_2AR$-transfected wild-type and presenilin-deficient MEFs (d) were treated for 30 min with the indicated reagents including 10 μM Iso, 10 μM Pro, 1 μM DADLE and 1 μM NALT respectively. The membrane fractions from cells or slice homogenates were subjected to fluorogenic substrate assay. Data are means±S.E. of at least three independent experiments and presented as fold values of the basal activity (*P<0.001). NALT, naltrindole.

To directly measure the enzyme activity of γ-secretase, a fluorogenic substrate was used. The fluorogenic substrate is based on the γ-secretase-specific substrate sequence conjugated with a fluorescent reporter molecules. It was found that γ-secretase activity was enhanced 30 min after stimulation of endogenous $\beta_2$AR in C6 glioma (FIG. 6b). This effect was confirmed in acute hippocampal slices (FIG. 6c). Presenilin-deficiency abolished the Iso-induced enhancement in mouse embryonic fibroblasts (FIG. 6d), confirming the specificity of this assay for γ-secretase activity. Taken together, these data clearly show that activation of $\beta_2$AR stimulates γ-secretase activity, leading to increased Aβ production.

Figure 7:
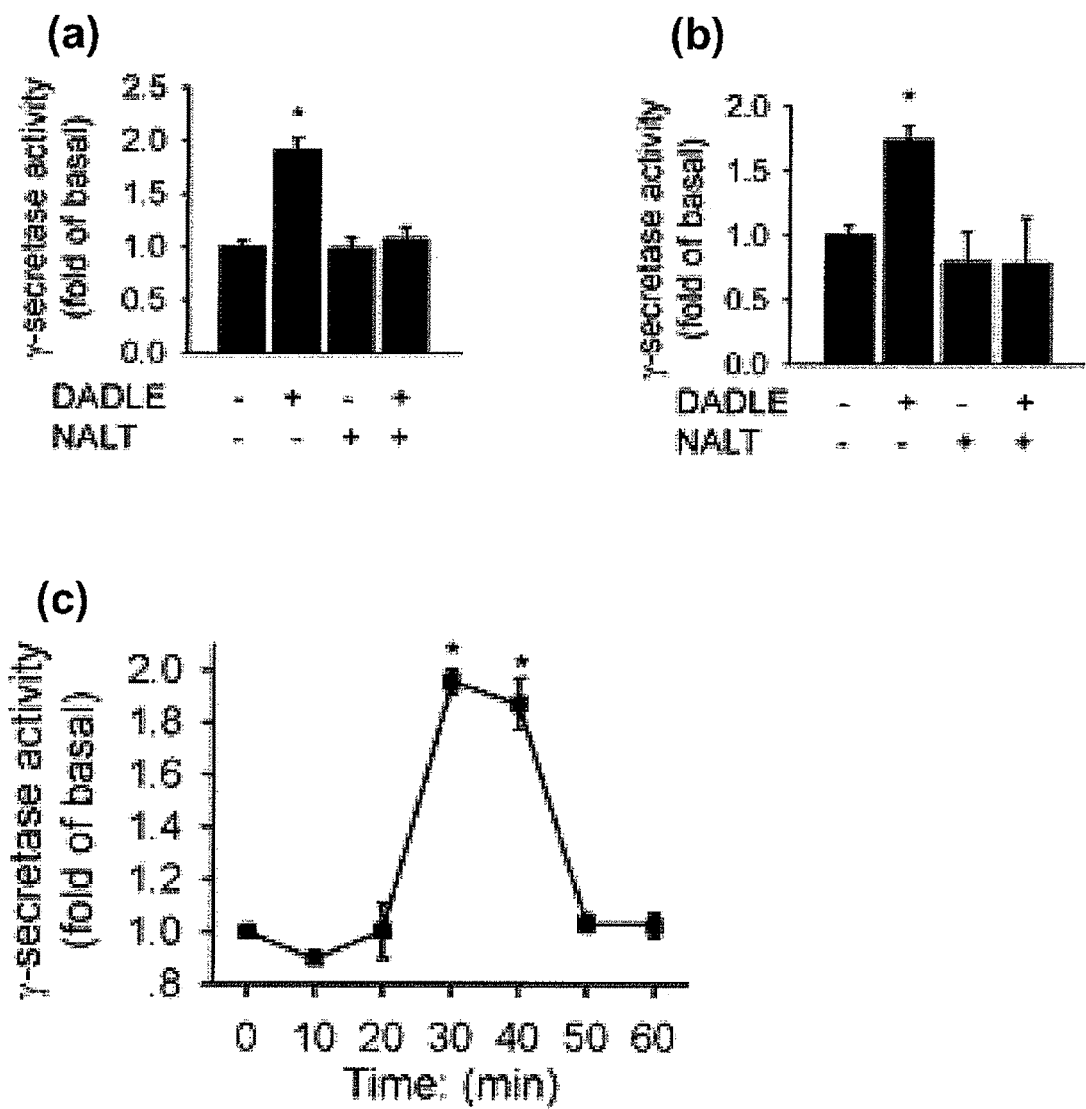
FIGS. 7A-7B show results of enhanced γ-secretase activity as a result of DOR activation, and time course of such enhancement. SH-SY5Y neuroblastoma (FIG. 7A) and acute hippocampal slices (FIG. 7B) were treated with 1 μM DADLE or 1 μM NALT for 30 minutes. The membrane fractions were subjected to fluorogenic substrate assay (*P<0.001).
FIG. 7C shows time course of g-secretase activity after activation of β2AR. C6 glioma were stimulated with 10 μM Iso for the indicated time. The cell membrane fractions were subjected to fluorogenic substrate assay (*P<0.01).

The enhancement of γ-secretase activity upon activation of receptors is not limited to β-AR. Similar results were also observed when endogenous DOR in SH-SY5Y neuroblastoma (FIG. 7a) or in primary hippocampal cultures (FIG. 7b) were stimulated. Furthermore, the results from the these γ-secretase assays showed that γ-secretase activity peaked at around 30 min and returned to the basal level at about 60 min after receptor (e.g., $\beta_2$AR) stimulation (FIG. 7c).

Example 3

Enhanced γ-Secretase Activity is Independent of cAMP Signaling

Figure 8:
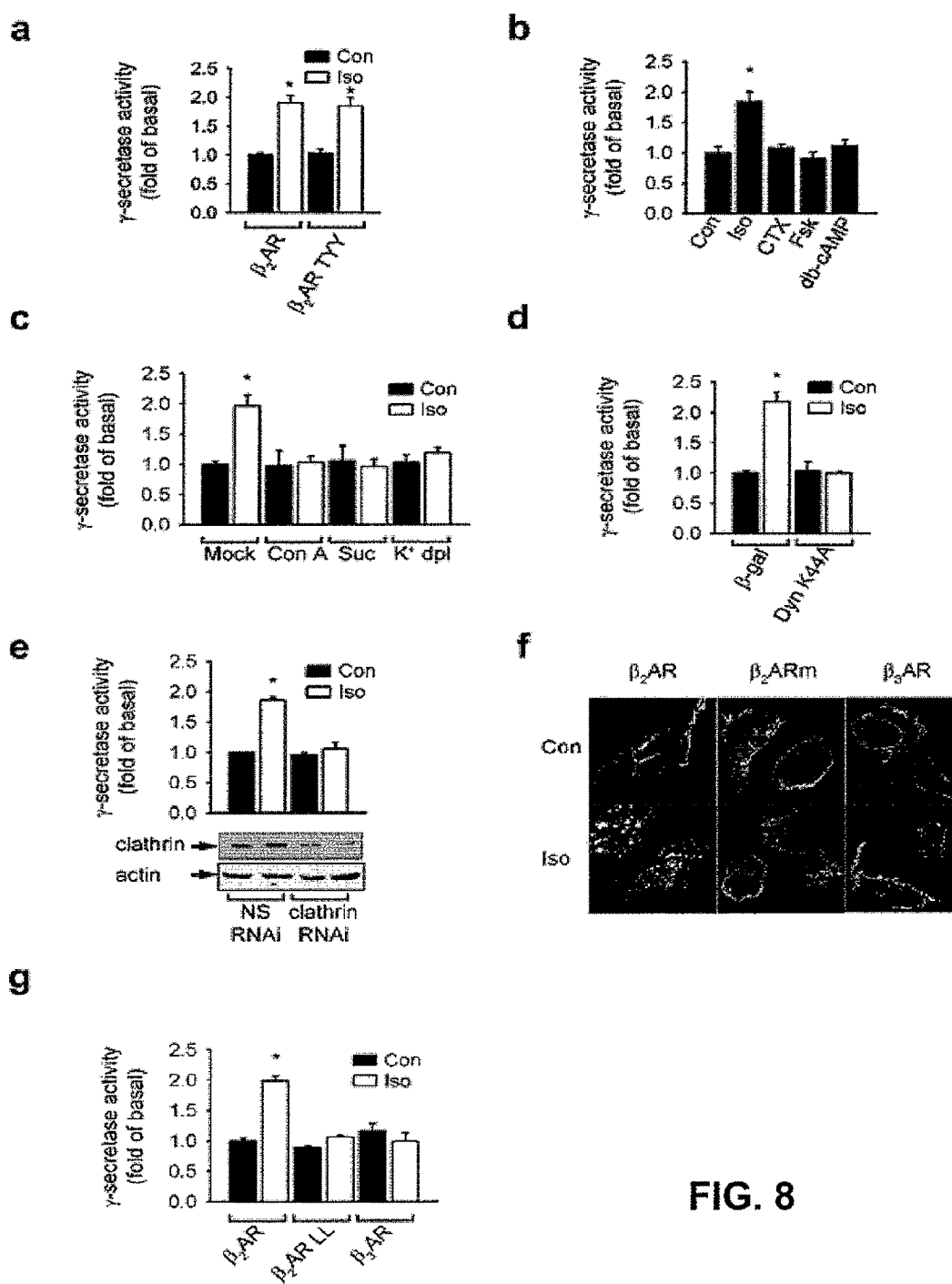
FIGS. 8a-8g show receptor endocytosis associates with enhanced γ-secretase activity. (a) HEK293 cells were transfected with $β_2AR$ or $β_2AR$ TYY and treated with 10 μM Iso for 30 min; (b) C6 glioma were treated for 30 min with the indicated reagents including 10 μM Iso, 1 μg/ml CTX, 10 μM Fsk, and 1 mM db-cAMP (left); (c) C6 glioma were treated for 30 min with 10 μM Iso after pretreatment with the indicated reagents including: 0.25 mg/ml Con A, 0.5 M Suc, and potassium depleted medium. (d) C6 glioma were transfected with β-gal or Dyn K44A and treated with 10 μM Iso for 30 min; (e) HEK293 cells were transfected with NS or clathrin RNAi and treated with 10 μM Iso for 30 min. The cell membrane fractions in (a to e) were subjected to fluorogenic substrate assay. (f and g) HEK293 cells transfected with the indicated receptors were treated for 30 min with 10 μM Iso and subjected to immunofluorescence assay (f) or fluorogenic substrate assay (g). Data in (a to e and g) are means±S.E. of at least three independent experiments and presented as fold values of the basal activity (*P<0.001). CTX, cholera toxin; Fsk, forskolin; db-cAMP, dybutyl cyclic adenosine monophosphate; PTX, pertussis toxin; Dyn K44A, dynamin II K44A; Con A, concanavalin A; Suc, hypertonic sucrose solution; K$^+$ dpl, potassium-depleted medium; NS RNAi, nonspecific RNA interference; $β_2ARm$, $β_2AR$ L339,340A.

As discussed above, once activated, GPCR (including $\beta_2$AR) may induce Gs protein-dependent adenyl cyclase activation, leading to elevated intracellular cAMP level. To delineate the molecular mechanism responsible for γ-secretase activity enhancement by $\beta_2$AR activation, a novel $\beta_2$AR mutant ($\beta_2$AR T68F, Y132G, Y219A or $\beta_2$AR TYY) incapable of Gs protein activation was used in a further study. It was found that these mutations of $\beta_2$AR failed to abolish the enhancement of γ-secretase activity (FIG. 8a). This result rules out the involvement of Gs protein signaling in the $\beta_2$AR effect on γ-secretase. Furthermore, cells treated with reagents such as cholera toxin (CTX), forskolin (Fsk), and dybutyl-cAMP (db-cAMP), which mimic G protein activation and cAMP level elevation, did not result in enhanced γ-secretase activity (FIG. 8b). Thus, the enhanced γ-secretase activities that result from β-adrenergic receptor activation do not involve cAMP signaling.

Figure 9:
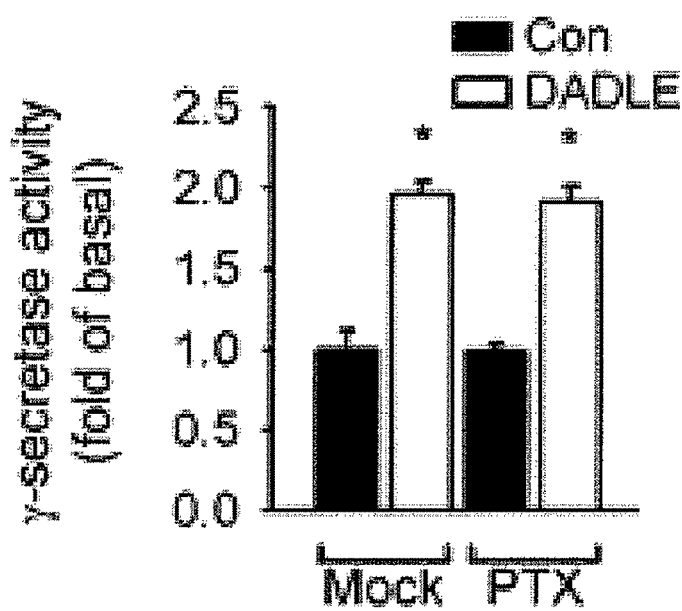
FIG. 9 shows the enhanced γ-secretase activity by DOR activation is not abolished by PTX treatment. SH-SY5Y neuroblastoma were stimulated with 1 μM DADLE after 12 hours pre-treatment with 200 ng/ml PTX. The cell membrane fractions were subjected to fluorogenic substrate assay (*P<0.01).

The fact that enhancement of γ-secretase activity does not involve cAMP signaling suggest that this might also be true for DOR. It is known that DOR activates pertussis toxin (PTX)-sensitive Gi/o protein, which then leads to decreased cAMP levels by inhibiting adenylyl cyclase. It was found that pre-treatment of SH-SY5Y neuroblastoma with PTX did not alter the enhancement of γ-secretase activity in response to DADLE stimulation (FIG. 9). This result suggests that enhancement of γ-secretase activity by DOR activation is also not regulated by cAMP. Therefore, regulation of γ-secretase by $\beta_2$AR or DOR activation does not rely on G protein signaling or the canonical cAMP pathway.

Example 4

Receptor Endocytosis Correlates with Enhanced γ-Secretase Activity

If the enhanced γ-secretase activity does not involve G-protein signaling nor the cAMP pathway, then what is the mechanism? As discussed above with reference to FIG. 3, GPCR (including PAR and opioid receptors) activation is often accompanied by receptor endocytosis, which can also initiate specific signaling. Whether receptor endocytosis and the associated signaling are involved in the enhanced g-secretase activity can be probed by using various inhibitors of the endocytosis pathway.

FIG. 8c shows that the effect of Iso on γ-secretase activity can be abolished by treatment with endocytosis inhibitors, such as concanavalin (Con A), hypertonic solution treatment (Suc), and potassium-depleted medium ($K^+$ dpl). FIG. 5d shows that the Iso-induced enhancement of γ-secretase activity can be abolished by transfection with a dominant negative version of dynamin (Dyn K44A) that inhibits clathrin- or caveolin-mediated endocytosis. As $\beta_2$AR mainly internalizes in a clathrin-dependent manner, small interfering RNA (RNAi) against clathrin heavy chain may be used to deplete cellular clathrin expression. FIG. 5e shows that the Iso-induced enhancement of γ-secretase activity could indeed by abolished by the RNAi. These results together show that $\beta_2$AR-induced enhancement of γ-secretase activity is mediated by signaling mechanisms associated with agonist-induced and clathrin-mediated endocytosis.

To further confirm the requirement of agonist-induced endocytosis of $\beta_2$AR for γ-secretase activity enhancement, the experiments were repeated with another mutant of $\beta_2$AR ($\beta_2$AR L339,340 A, or β2AR LL) as well as another intrinsic adrenergic receptor $\beta_3$AR, both of which are deficient in agonist-induced endocytosis. It was found that stimulation of these receptors in HEK293 cells resulted in neither receptor endocytosis (FIG. 8f), nor enhanced γ-secretase activity (FIG. 8g), though elevation of the cAMP level did occur (data not shown). These results clearly show that agonist-induced and clathrin-mediated endocytosis of $\beta_2$AR is involved in the enhancement of γ-secretase activity.

Figure 10:
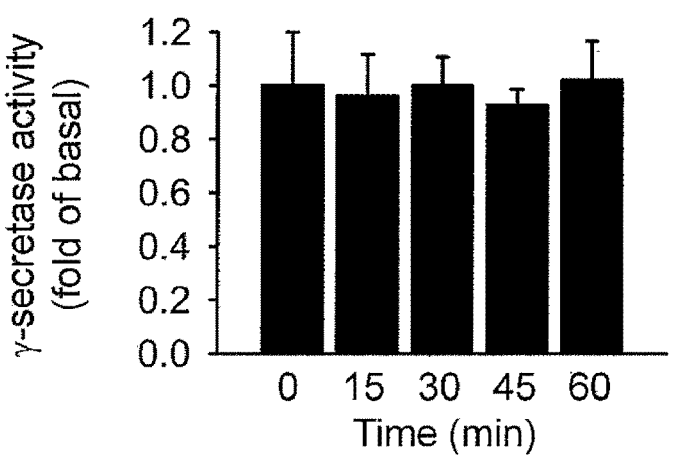
FIG. 10 shows receptor endocytosis induced by transferrin does not lead to enhanced γ-secretase activity.

The above experiments show that clathrin-mediated endocytosis is necessary for the enhancement of γ-secretase by receptor activation. However, it is till not clear whether clathrin-mediated endocytosis by itself is insufficient to induce the enhancement of γ-secretase activity. To answer this question, HEK293 cells were treated with transferrin, which can induce constitutive clathrin-dependent endocytosis of transferrin receptor. As shown in FIG. 10, transferring treatment failed to enhance γ-secretase activity, even though it can induce constitutive endocytosis. These results suggest that clathrin-mediated endocytosis is necessary, but not sufficient, for $\beta_2$AR-induced enhancement of γ-secretase activity.

Example 5

Enhanced γ-Secretase Activity and Aβ Production Associate with Endocytic Pathway As shown in FIG. 3, once inside the cell, the endocytic vesicles are transported to their destinations via specific endocytic pathways. The endocytic pathways involve trafficking of intracellular compartments that are regulated by Rab guanosine triphosphatases (Rab GTPase). It is known that endocytic transports from plasma membrane to early endosomes and then to LEL can be blocked by Rab5 S34N or Rab7 T22N, which are dominant negative mutants of early endosome marker Rab5 or LEL marker Rab7, respectively. As shown in FIG. 11a and FIG. 11b, expression of Rab5 S34N or Rab7 T22N in HEK293 cells abolished $\beta_2$AR-stimulated enhancement of γ-secretase activity (FIG. 11a) and Aβ production (FIG. 11b). Since the Rab7 T22N transfected cells can still have endocytic vesicles transported to the early endosomes. These results suggest that the enhanced γ-secretase activity and Aβ production require the endocytic vesicles to be transported to the LEL, indicating that LEL is critically involved in the effects of $\beta_2$AR on γ-secretase activity and Aβ production.

To further show the involvement of LEL, LEL vesicles were immuno-isolated from Flag-Rab7-transfected cells with Flag antibody, and subsequently verified by blotting the isolates with an early endosome marker, early endosome antigen 1 (EEA1), or an LEL marker, lysosome-associated membrane protein-1 (LAMP-1). As shown in FIG. 11c, the amount of Aβ, but not Flag-Rab7 or LAMP-1, in the LEL was markedly increased after 1-h $β_2$AR stimulation, indicating that Aβ production in the LEL was enhanced by $β_2$AR activation without increasing the amount of LEL.

Figure 12:
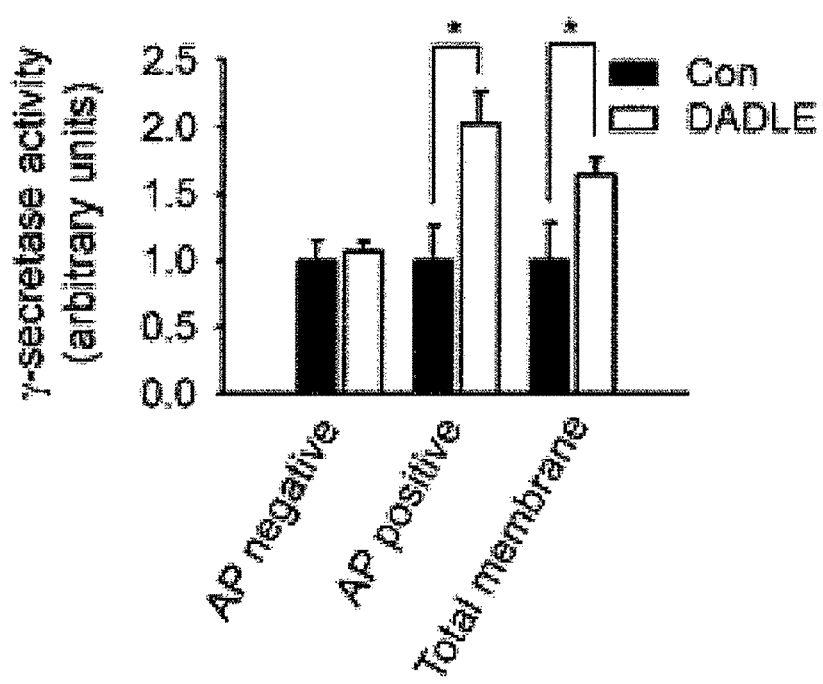
FIG. 12 shows the enhanced γ-secretase activity by DOR activation is also associated with LEL fractions.

Again, the involvement of LEL in the enhancement of the γ-secretase activity is not limited to β-AR. FIG. 12 shows that γ-secretase activity in the LEL was also enhanced after DOR stimulation. The experiment shown in FIG. 12 was performed with SH-SY5Y neuroblastoma. These cells were treated with 1 μM DADLE for 30 minutes and then fractionated. The fractions were subjected to alkaline phosphatase (Aβ) assay and fluorogenic substrate assay. The results clearly show that DADLE treatment enhanced the γ-secretase activity in the AP positive fraction (*P<0.01), but not in the AP negative fraction.

Figure 11:
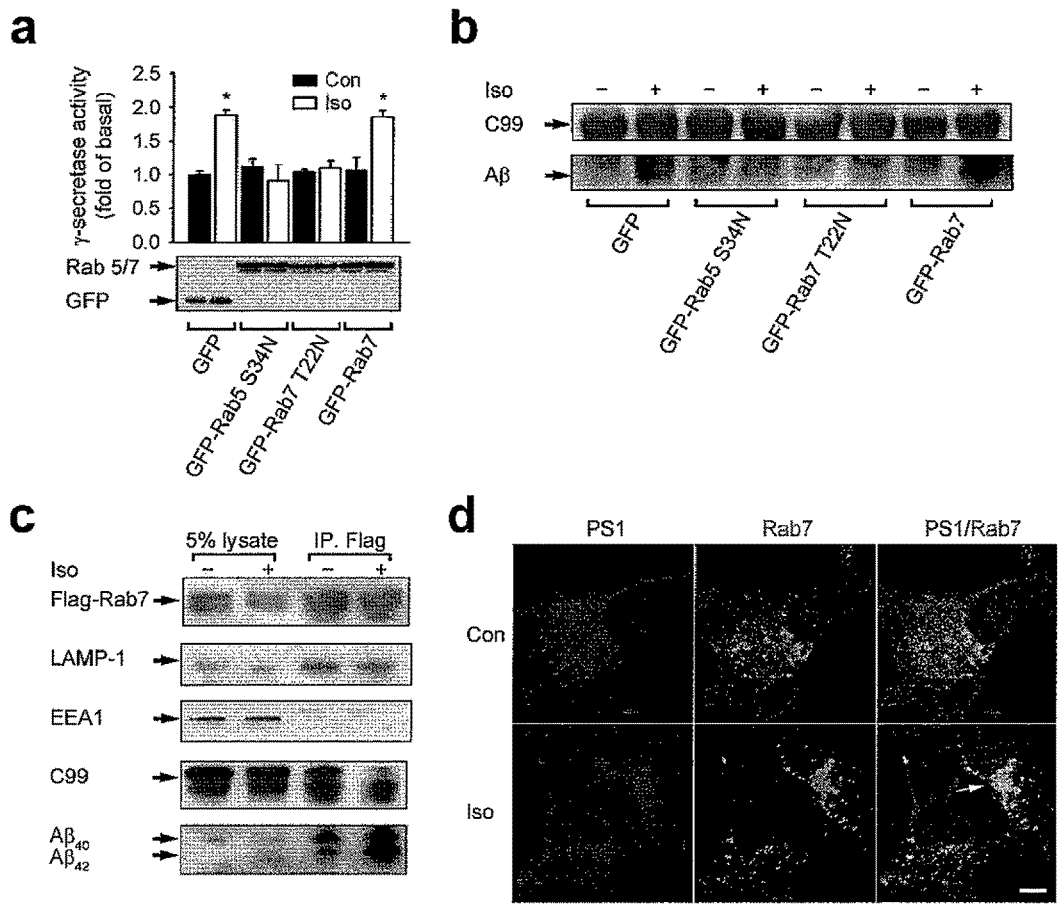
FIGS. 11a-11d show increased γ-secretase and Aβ in endocytic compartments. (a) HEK293 cells co-transfected with $β_2AR$ and the indicated plasmids in combination with or without C99, were treated with 10 μM Iso. The membrane and cytoplasma fractions were subjected to fluorogenic substrate assay (*P<0.001) or Western blot, respectively. (b) HEK293 cells were transfected and treated as in (a). The cytoplasma fractions were subjected to Aβ-specific immunoprecipitation/Western blot. (c) HEK293 cells co-transfected with $β_2AR$, C99 and Flag-Rab7, were treated for 1 h with 10 μM Iso. The cell homogenates were subjected to immuno-isolation of LEL and Western blot using specific antibodies for the indicated proteins. Data are representative of at least three independent experiments. (d) HEK293 cells co-transfected with HA-$β_2AR$ and GFP-Rab7 were treated for 30 min with 10 μM Iso and detected for the distribution of PS1 (red), GFP-Rab7 (green), and $\beta_2$AR (blue). Arrows mark the punctual structures containing PS1 and GFP-Rab7.

Taken together, the results shown in FIG. 11 and FIG. 12 suggest that the LEL plays a critical role in the effects of $β_2$AR or DOR activation on Aβ production. These observations confirm that endocytic compartments can provide optimal environments for γ-secretase activity.

To further confirm that γ-secretase in the LEL is associated with the increased Aβ production, immunofluorescence microscopy was used to examine whether localization of γ-secretase in the LEL is promoted by β2AR stimulation. For experiments in cell lines, LEL was marked with the expressed GFP-Rab7. FIG. 11d shows that co-localization of PS1 (γ-secretase active site subunit) with GFP-Rab7 occurred in HEK293 cells 30 min after $β_2$AR stimulation in transfected HEK293 cells. For acute hippocampal slices, LEL was marked with LAMP-1 by using specific antibody. FIG. 11e shows that co-localization of PS1 or nicastrin (another γ-secretase component) with LAMP-1 increased after Iso treatment. Together the above results suggest that $β_2$AR stimulation promotes the localization of γ-secretase to the LEL, which in turn leads to enhanced γ-secretase activity and Aβ production.

Example 6

Constitutive Association Between PS1/γ-Secretase and $β_2$AR

Figure 13:
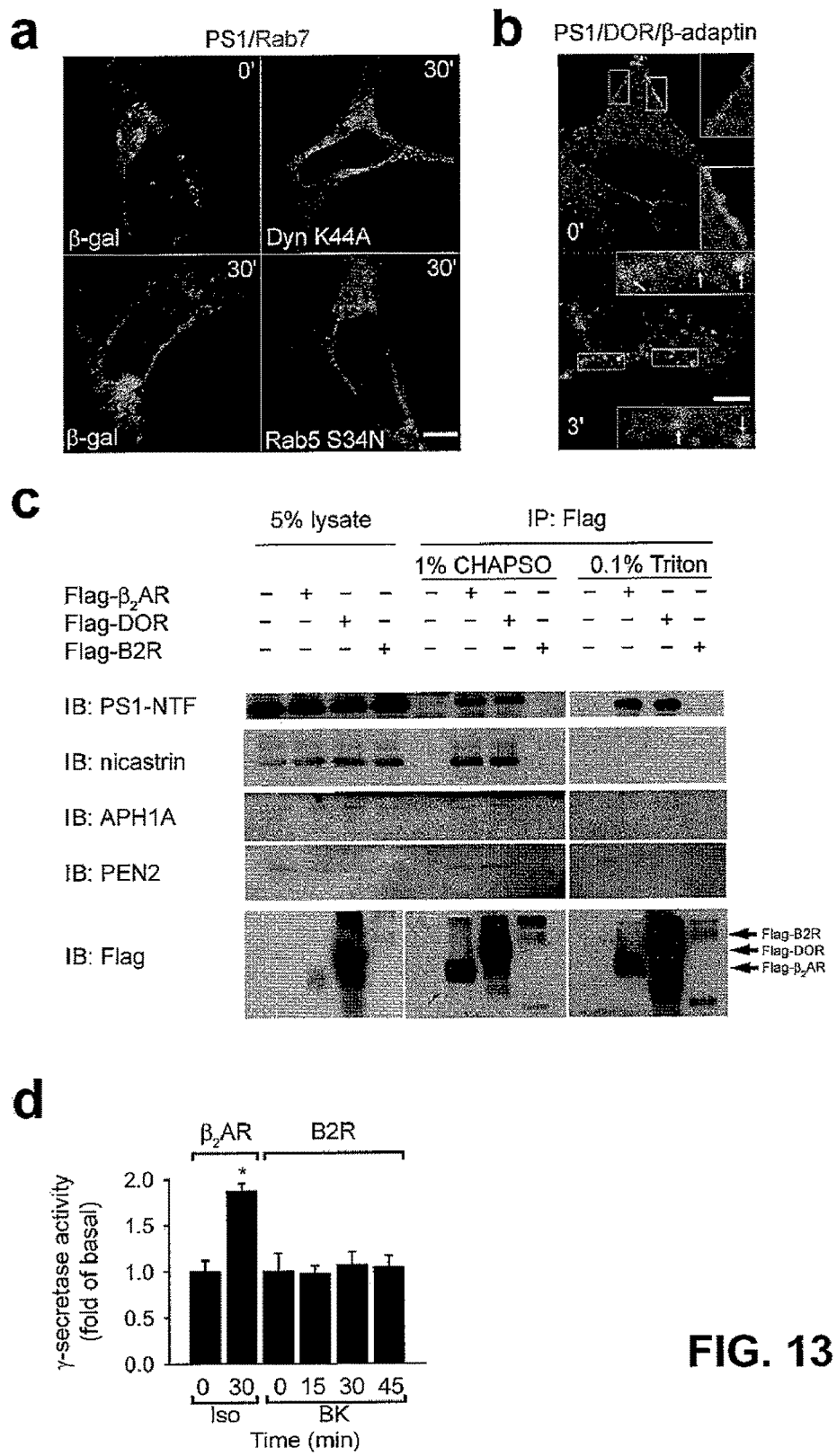
FIGS. 13a-13d show γ-secretase enrichment requires endocytic transport. (a) HEK293 cells transfected with HA-$\beta_2$AR and Flag-Rab7 in combination with P-gal, Dyn K44A or Rab5 S34N, were treated with 10 μM Iso for 30 min, stained with antibodies against PS1-NTF (red) or Flag (green). Scale bar, 8 μm. (b) HEK293 cells transfected with HA-DOR were treated with 1 μM DADLE for 3 min, stained with antibodies against PS1-NTF (red), DOR (green) and β-adaptin (blue). Arrows mark the punctual structures containing PS1, DOR and β-adaptin (insets). Scale bar, 8 μm. (c) HEK293 cells transfected with HA-$\beta_2$AR, HA-DOR or HA-B2R were subjected to immuno-precipitation with buffer containing 0.1% Triton X-100 (left) or 1% CHAPSO (right), and the immunoprecipitates and 5% whole cell lysates were immunoblotted with the indicated antibodies. Data are representative of at least three independent experiments. (d) HEK293 cells transfected with $\beta_2$AR or B2R were treated with 10 μM Iso or 1 μM BK. The membrane fractions were subjected to fluorogenic substrate assay (*P<0.001). Con, control; Dyn K44A, dynamin II K44A; IB, immuno-blot. BK, bradykinin.

The finding that co-expression of Dyn K44A or Rab5 S34N effectively prevented the elevated localization of PS1 in LEL following $β_2$AR stimulation (FIG. 13a) suggests that PS1 may be transported to LEL from the plasma membrane. Using P-adaptin, which specifically marks clathrin-coated pits and vesicles, it was found that co-localization of PS1 with O-adaptin and the endocytosed receptor after 3-min stimulation of DOR in HEK293 cells (FIG. 13b). These findings imply the co-endocytosis of PS1 and the activated receptor after agonist stimulation of $β_2$AR or DOR. This is not surprising because PS1 constitutively interacts with membrane proteins, such as APP and Notch, and $β_2$AR can mediate the endocytosis of other transmembrane proteins by forming heterodimers with the latter. To show that this is the case, the association between PS1 and $β_2$AR or DOR was examined with co-immunoprecipitation assays.

As shown in FIG. 13c, the four essential γ-secretase components, PS1, nicastrin, anterior pharynx defective-1a (APH-1a) and presenilin enhancer-2 (PEN-2), were co-precipitated with $β_2$AR or DOR in the CHAPSO-containing buffer (left panel in FIG. 13c), in which γ-secretase stays as a complex. Replacement of CHAPSO with Triton X-100, which is known to dissociate γ-secretase complex, disrupted the co-precipitation of receptors with nicastrin, APH-1a and PEN-2, but not PS1, as detected with PS1-NTF or PS1-CTF antibodies (middle panel of FIG. 13c). These results suggest that $β_2$AR and DOR associate with γ-secretase via direct binding to PS1. However, such associate does not occur with every GPCR because another member of GPCRs, B2 bradykinin receptor (B2R), failed to associate with PS1/γ-secretase (FIG. 13c, right) or induce γ-secretase activity (FIG. 13d). Taken together, these results suggest that the $β_2$AR-PS1 or DOR-PS1 association was specific and provided a mechanistic base for the enhancement of γ-secretase activity by activation of these receptors. In addition, these results suggest that reagents that can disrupt or weaken receptor-PS1 associations are potential therapeutic agents for the treatment or prevention of Alzheimer or related neurological diseases.

Example 7

Screening of Reagents that can Disrupt or Weaken the Association Between PS1 and Receptors Reagents that can disrupt or weaken the association between PS1 and receptors may be screened with any suitable method, such as FRET (fluorescence resonance energy transfer). FRET is a process in which energy is transferred from an excited donor fluorophore to an acceptor fluorophore via short-range ($\leq 10$ nm) dipole-dipole interactions. Thus, FRET can be used to detect physical interactions between two binding proteins. In FRET, the non-radiative transfer of energy attenuates light emission from the donor. Thus, FRET may be detected, for example, by comparing the intensities of light emission from the donor in the same sample before and after destroying the fluorescent moiety on the acceptor by a suitable method, such as photo-bleaching. If FRET is present, donor emission will be more intense after photo-bleaching of the acceptor.

In one example, changes in FRET efficiencies between GFP-DOR and PS1-Cy3 before and after PS1-Cy3 photo-bleaching were detected in co-transfected HEK293 cells. The cells were co-transfected with GFP-DOR and HA-ps1. HA-PS1 expression may be identified by adding a primary antibody against HA and a second antibody conjugated with fluorophore, Cy3 (Jackson ImmunoResearch), while GFP-DOR expression may be identified by GFP fluorescence.

FIGS. 23A-23C show results from one such experiment. The images, which were obtained with a Leica confocal microscope, include mixed emission spectra of the GFP-DOR donor and PS1-Cy3 acceptor fluorophores (excitation with a 488 nm laser). First, it was examined whether the emission of light by the donor (GFP-DOR) became more intense after photo-bleaching of the acceptor (PS1-Cy3) when two proteins were co-expressed in HEK293 cells. FIG. 23A shows images taken from the photo-bleached and non-photo-bleached regions of the cell before and after localized photo-bleaching. The selected regions were photo-bleached with a 561 nm laser, which is within the absorption spectrum of Cy3. The intensity corresponding to GFP-DOR emission was substantially higher in the photo-bleached region, as compared to the non-photobleached region in the same cell. These results indicated that FRET occurred between GFP and Cy3, and such energy transfer is abolished or reduced upon photo-bleaching of Cy3.

Figure 23:
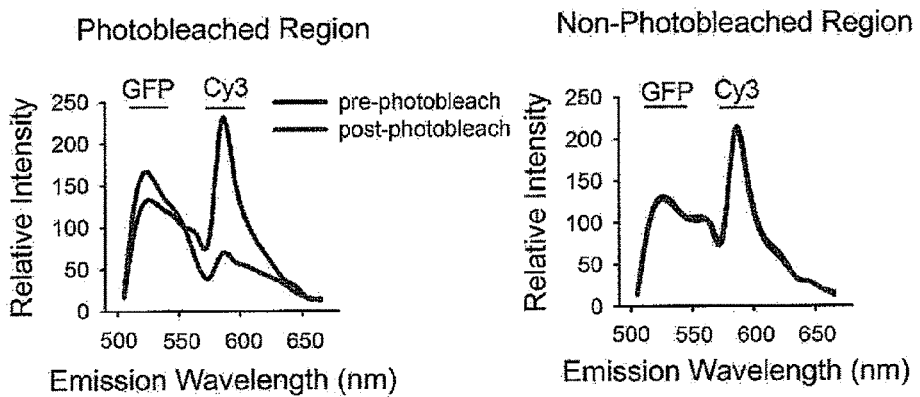
FIG. 23A-23C show results of surface-associated DOR receptor binding to PS1.
Figure 23:
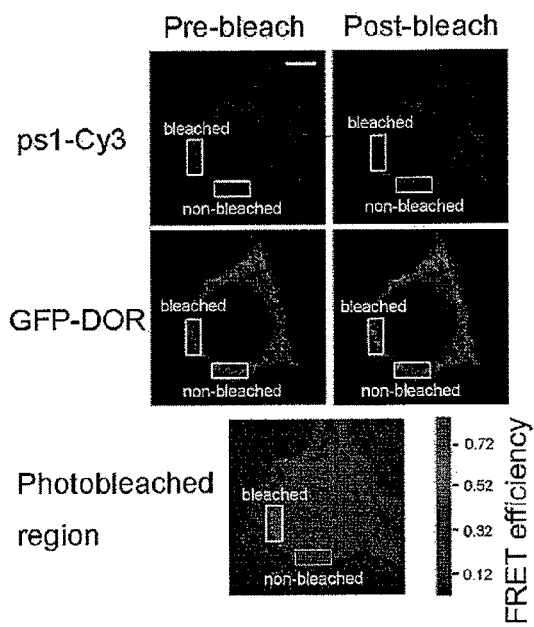
Figure 23:
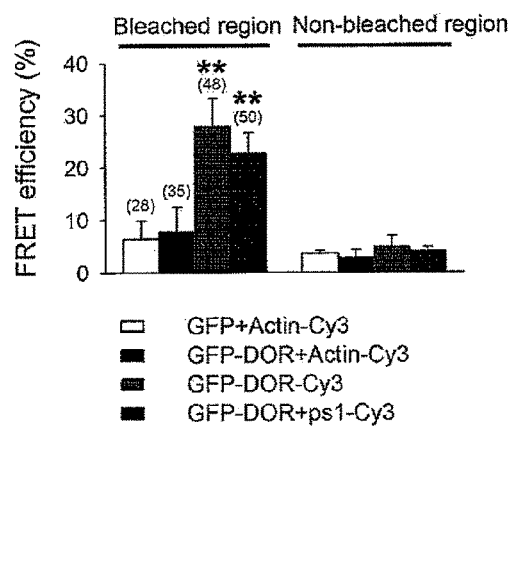

FIG. 23 B shows a representative set of individual images (GFP-DOR or PS1-Cy3) from the transfected HEK293 cells was illustrated before and after photo-bleaching of the acceptor with 561 nm laser. The GFP-DOR images showed an increase in the donor emission (pseudocolored intensity images) after photo-bleaching, and this increase occurred only in the region of the cell exposed to the photo-bleaching.

As shown in FIG. 23C, the averaged relative FRET efficiencies between the associated GFP-DOR and PS1-Cy3 near the surface region were found to be around 22.8±3.9%, which serves as an indicator of their interaction. In the positive control, the cells expressing GFP-DOR were incubated with a primary antibody against GFP and a second antibody conjugated with Cy3. This positive control showed a FRET efficiency 27.9±5.3%. As a negative control, the cells expressing GFP-DOR were incubated with a primary antibody against actin and a second antibody conjugated with Cy3. This negative control showed a FRET efficiency 7.8±4.7%. These data together suggest that DOR receptor associates with PS1.

Example 8

Figure 14:
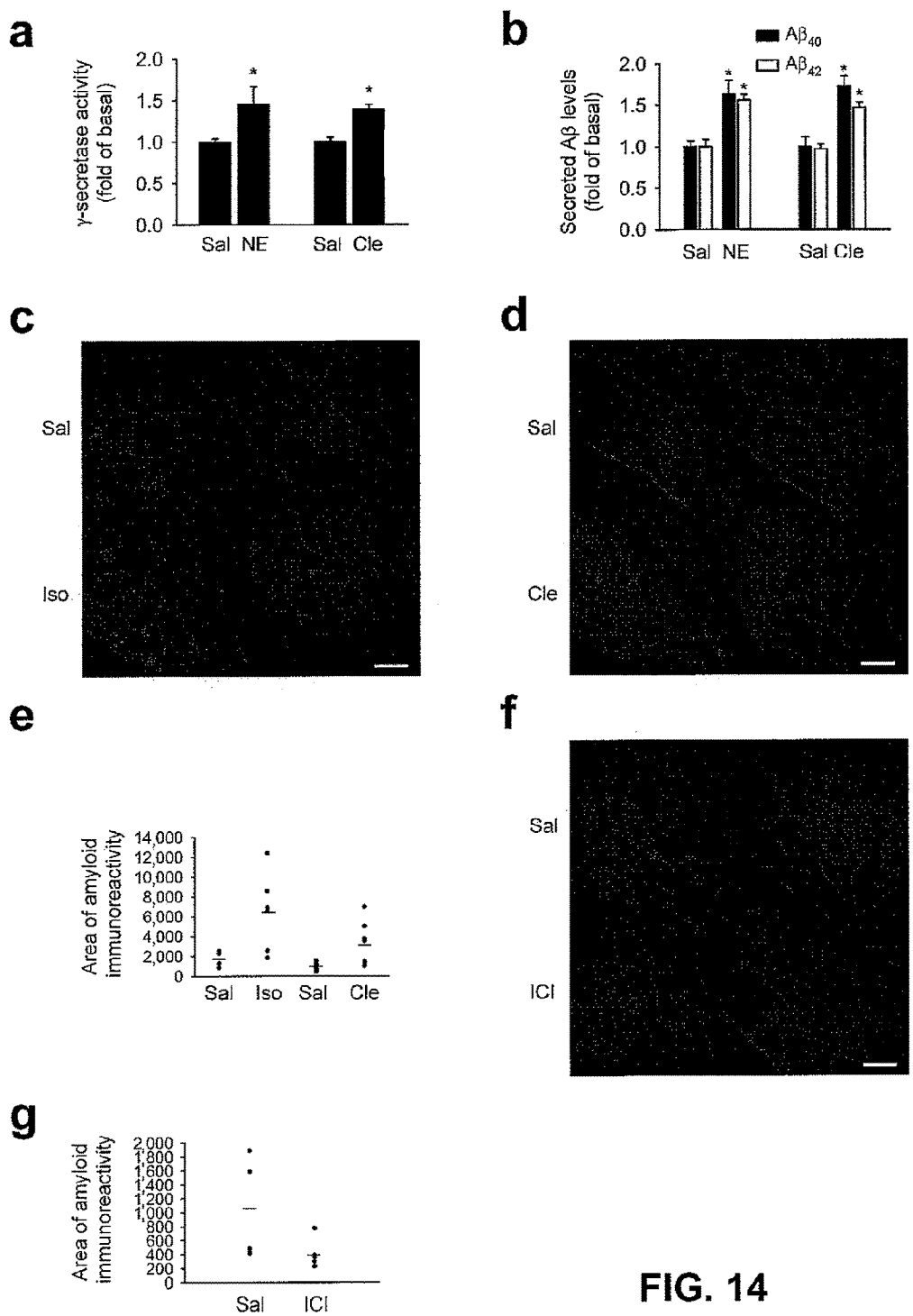

Enhanced γ-Secretase Activity, Aβ Production, and Amyloid Plaque Formation in Animals The effects of $\beta_2AR$ on these AD-linked molecules were further investigated in animals. The in vivo experiments showed that both the γ-secretase activity (FIG. 14a) and Aβ levels (FIG. 14b) in rat hippocampus were significantly enhanced by acute injection of an endogenous ligand for adrenergic receptors (norepinephrine, NE) or a known $\beta_2AR$-selective agonist clenbuterol (Cle). Based on these results, it can be expected that chronic exposure to agonists of these receptors may worsen AD-related pathology in animal models. Experiments in an AD mouse model (APPswe/PS1ΔE9 double-transgenic mice) support this idea, as those mice displayed increased cerebral amyloid plaques after chronic administration of Iso or Cle for 30 days (FIGS. 14c-14e). This observation indicates that activation of $\beta_2AR$ can enhance γ-secretase activity, Aβ production, and amyloid plaque formation. Therefore, antagonists of these receptors should be useful in reducing Aβ or amyloid plaque formation. FIGS. 14f and 14g show that this is indeed the case, as ICI 118,551, a β2AR specific antagonist, significantly reduced the amounts of amyloid plaques.

Example 9

In Vivo Animal Model Studies

To assess the in vivo effectiveness of β-adrenergic receptor antagonists, such compounds were administered to a transgenic mouse model of Alzheimer's disease (APPswe/PS1ΔE9). At about 6 months of age, these mice would have progressive spatial memory deficits that are accompanied by rising cerebral Aβ levels and increasing numbers of cerebral amyloid plaques.

In the following studies, APPswe/PS1ΔE9 mice and non-transgenic NTg) littermates were assigned to sex- and age-matched cohorts. Test compounds were orally administered, beginning at 4 months of age and continuing for one or two months. The effects of various compounds on the APPswe/PS1ΔE9 and non-transgenic mice were then assessed with the Morris water maze tests.

The Morris water maze test developed by neuroscientist Richard G. Morris in 1984 is commonly used today to explore the role of hippocampus in the formation of spatial memories. The maze used in the experiments was a circular pool (diameter 1.2 m) filled with water at 24-25° C., which was made opaque by the addition of milk powder. The pool was placed among fixed spatial cues consisting of boldly patterned curtains and shelves containing distinct objects. During the tests, mice were gently lowered into the water, facing the wall of the pool. Mice first underwent visible platform training for a selected number of sessions (e.g., 2 consecutive days with eight trials per day), swimming to a raised circular platform (10 cm diameter) marked with a pole-Visible platform trainings were split into two training blocks (e.g., four trials per day) for statistical analysis. During the visible platform training, both the platform location (NE, SE, SW, or NW) and start position (N, E, S, or W) were varied pseudo-randomly in each trial.

Hidden platform training was conducted over a selected number of days (e.g., 6 consecutive days, four trials per day), wherein mice were allowed to search for a platform submerged 1.5 cm beneath the surface of the water. Mice failing to reach the platform within 60 sec were led to the platform. During the hidden-platform trials, the location of the platform remained constant, and mice entered the pool in one of the four pseudo-randomly selected locations (N, E, S, or W). After each hidden platform trial, mice remained on the platform for 30 see and were removed from the platform and returned to their home cage.

Twenty-four hours after the final hidden platform training, a probe trial was conducted in which the platform was removed from the pool and mice were allowed to search for the platform for 60 sec. All trials were monitored by a camera mounted directly above the pool and were recorded and analyzed using a computerized tracking system.

Animal Model Experiment 1

In one experiment, propranolol and nadolol were administered to APPswe/PS1ΔE9 transgenic and non-transgenic (NTg) mice to assess the effects of β-adrenergic receptor antagonists on amyloid plaque formation. APPswe/PS1ΔE9 mice and non-transgenic (NTg) littermates were assigned to sex- and age-matched cohorts. Compounds were orally administered, with beginning at 4 months of age and continuing until 6 months of age. Propranolol can readily cross the blood-brain barrier (BBB), and, therefore, it can antagonize β-adrenergic receptor of the central nervous system. On the other hand, nadolol, which is also a β-adrenergic receptor antagonist, cannot cross the BBB. The mice were tested with spatial learning and memory using a Morris water maze.

In the Morris water maze task, mice were first subjected to two days of visible platform training, with two blocks of training each day. In each block of training, the latency of mice to find and climb onto the platform was recorded. No genotype or drug effect was found on this training ($P=0.101$, FIG. 15a).

Next, mice were subjected to six days of hidden platform training with one block of training each day. The control mice showed significant impairment as compared to the non-transgenic mice ($P<0.001$, FIG. 15b). While propranolol treatment partially ameliorates the impairment of the treated mice as compared to control mice ($P=0.039$), nadolol treatment showed no effect ($P=0.222$).

Finally, mice were subjected to a probe trial 24 h after the final hidden platform training. In this trial, mice were allowed to freely swim without a platform for 1 min. The percentage of time spent by mice in the platform quadrant was analyzed (FIG. 15c). Again, there was a significant genotype effect between transgenic mice and non-transgenic control mice ($P<0.001$). Propranolol treatment partially ameliorated the impairment of spatial memory in the transgenic mice ($P=0.021$), while nadolol had no effect ($P=0.703$). While propanolol showed effects in the platform tests, these effects did not result from difference in swim speeds (FIG. 15d).

The above study clearly shows that propranolol can antagonize β-adrenergic receptors in the central nervous system. Because propranolol is a non-selective β-adrenergic antagonist, subtype-selective β-adrenergic receptor antagonists are examined in vivo to determine which subtype is responsible for the above observed effects. The subtype-selective β-adrenergic receptor antagonists examined include Betaxolol and ICI 118,511. Betaxolol is a β1AR-selective antagonist that can cross the BBB. ICI 118,551 is a β2AR-selective antagonist that can cross the BBB.

Figure 16:
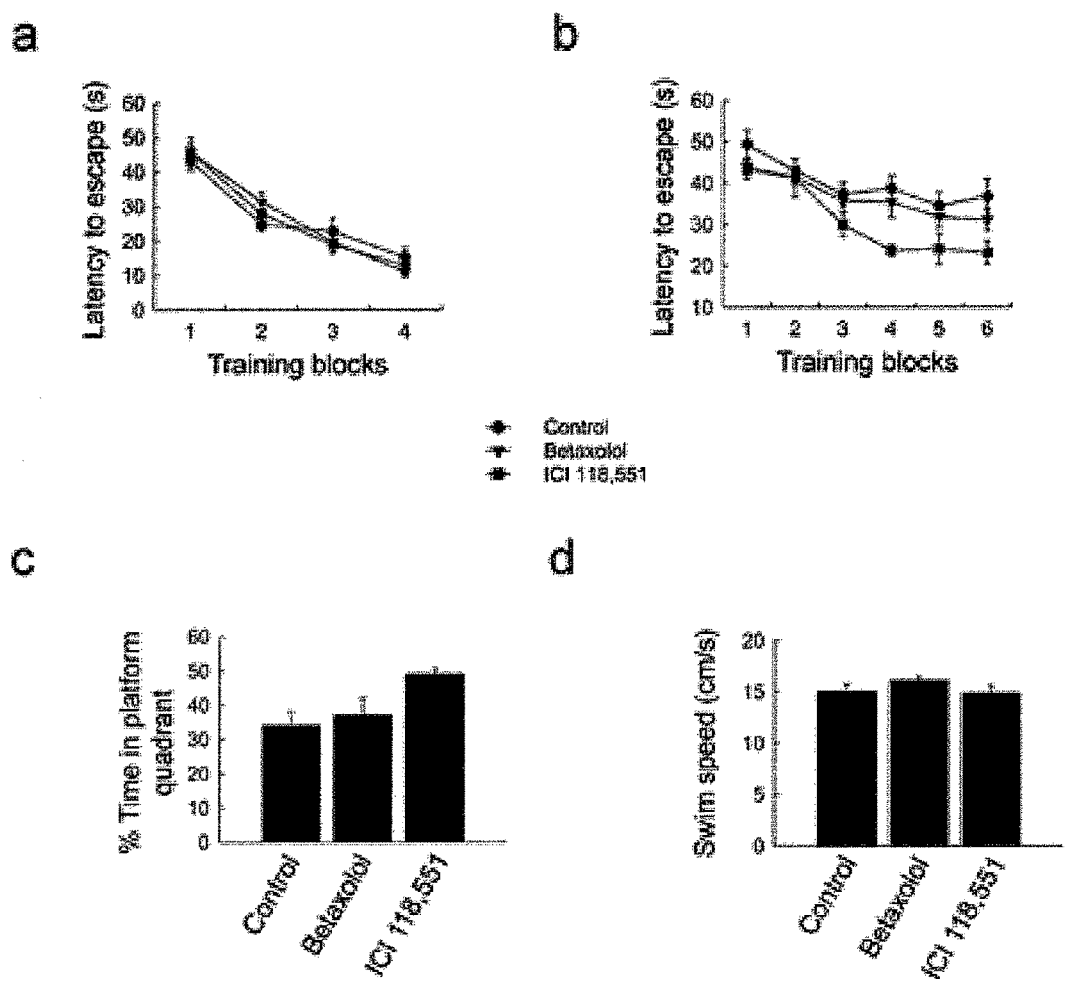
FIGS. 16a-16d show results from animal test similar to those in FIG. 15, but with receptor subtype specific antagonists. Betaxolol is a β1AR-selective antagonist that can cross the BBB. ICI 118,551 is a β2AR-selective antagonist that can cross the BBB. (a) In the visible platform training, no drug effect was observed (F=0.0310, P=0.969). (b) In the hidden platform training, ICI 118,551 treatment significantly ameliorated cognitive impairment (F=24.164, P<0.001). Betaxolol showed some extent of amelioration, but the effect was not statistically significant (F=3.698, P=0.057). (c) In the probe trial, the effect of ICI 118,551 was significant (P=0.005). Betaxolol showed no effect (P=0.552).

In the visible platform training, no drug effect was observed (FIG. 16a, P—0.747). However, in the hidden platform training (FIG. 16b), ICI 118,551 treatment significantly ameliorated cognitive impairment (P<0.001). Betaxolol showed some effect; however, this effect was not as significant (P=0.071) as that of ICI 118,511. In the probe trial (FIG. 16c), the effect of ICI 118,551 was significant (P<0.001). Again, Betaxolol showed less significant effect (P=0.391), as compared to that of ICI 118,511. Effects of propranolol ICI 118,551 did not result from changes in swim speeds (FIG. 16d).

Figure 17:
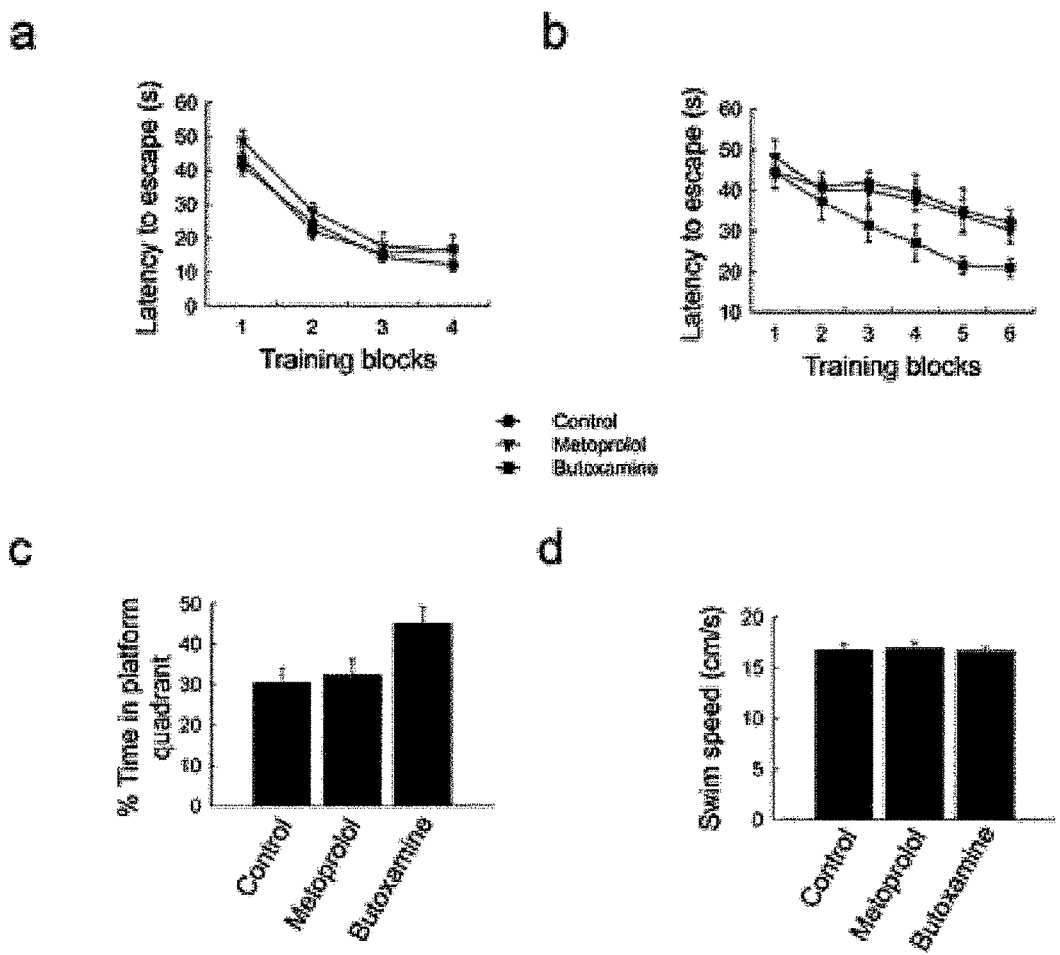
FIGS. 17a-17d show results from animal test similar to those in FIG. 16. Metoprolol is a β1AR-selective antagonist that can cross the BBB. Butoxamine is a β2AR-selective antagonist that can cross the BBB. (a) In the visible platform training, no drug effect was observed (F=2.017, P=0.139). (b) In the hidden platform training, Butoxamine treatment significantly ameliorated cognitive impairment (F=15.581, P<0.001). Metoprolol showed no effect (F=0.104, P=0.748). (c) In the probe trial, the effect of butoxamine was significant (P=0.020). Metoprolol showed no effect (P=0.768).

That β2AR selective antagonists are more effective is corroborated by a further experiment comparing another pair of antagonists specific to β1AR and β2AR, respectively. FIGS. 17a-17d show results from animal test similar to those in FIG. 16. Metoprolol is a β1AR-selective antagonist that can cross the BBB. Butoxamine is a β2AR-selective antagonist that can cross the BBB. As shown in FIG. 17a, in the visible platform training, no drug effect was observed (F=2.017, P=0.139). However, in the hidden platform training, Butoxamine treatment significantly ameliorated cognitive impairment (F=15.581, P<0.001), as shown in FIG. 17b. In contrast, metoprolol showed no effect (F=0.104, P=0.748). FIG. 17c shows that in probe trials, the effect of butoxamine was significant (P=0.020), whereas metoprolol had no effect (P=0.768). Again, the observed effects were not due to difference in swim speeds, as shown in FIG. 17d.

Taken together, the above results indicate that β-adrenergic receptor antagonists target primarily central nervous β-adrenergic receptors (β-AR) to achieve the enhanced γ-secretase activity and reduced Aβ production. Furthermore, most of the desired effects to ameliorate spatial memory deficits can be achieved by inhibition of β2AR, while inhibition of β1AR produce less effects. Thus, in accordance with embodiments of the invention, β-AR antagonists to be used for prevention or treatment of Alzheimer's disease are preferably those acting on β2AR.

Figure 18:
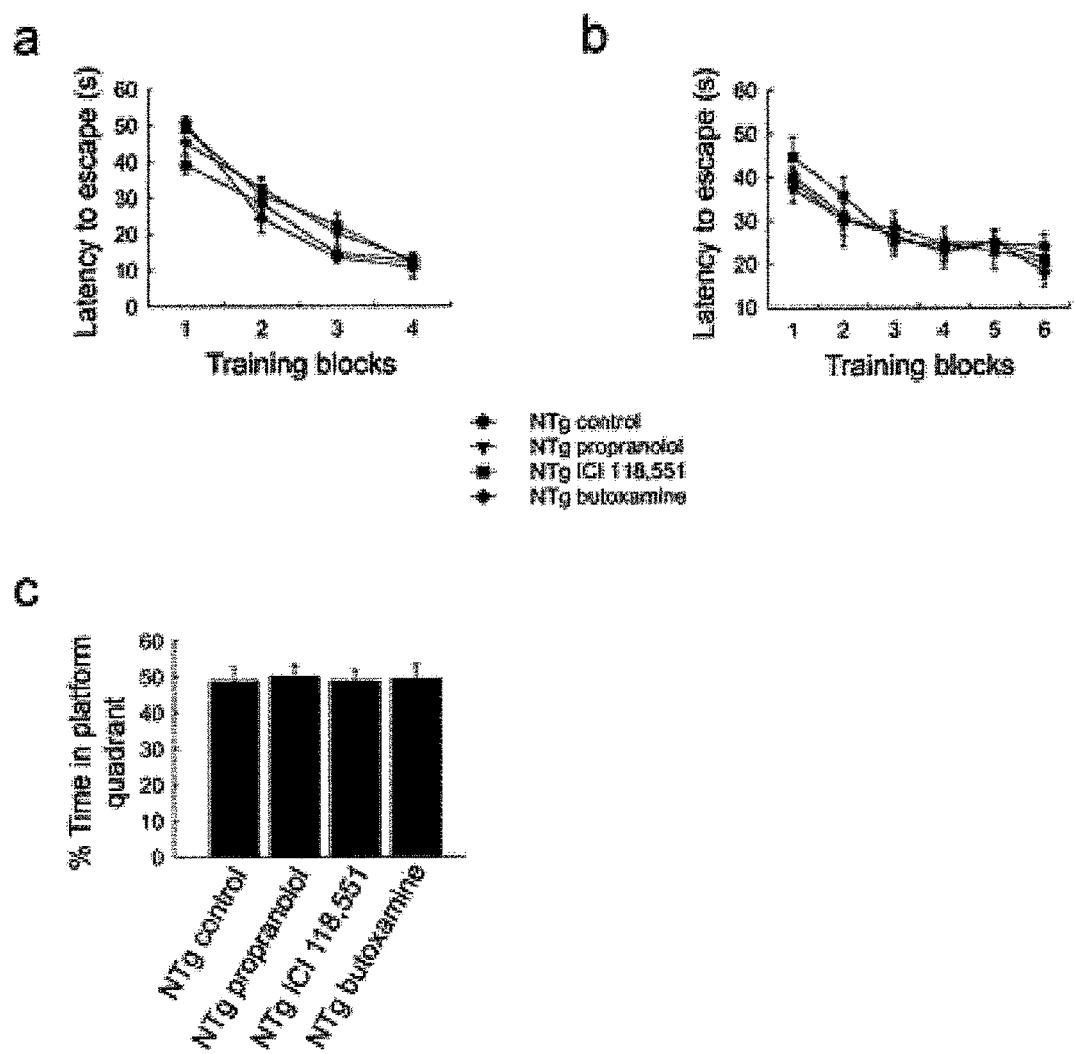
FIG. 18 shows results from non-transgenic mice. β-adrenergic receptor antagonists showed no effect on non-transgenic mice, suggesting that transgenes are essential. (a) no drug effect was observed in the visible platform training (F=2.327, P=0.077). (b) no drug effect was observed in the hidden platform training (F=0.264, P=0.851). (c) no drug effect was observed in the probe trial (P=0.817).

In further experiments, it was found that these β-adrenergic receptor antagonists showed no effect on non-transgenic mice. As shown in FIG. 18, no drug effect was observed in the visible platform training (FIG. 18a, P=0.054), the hidden platform training (FIG. 18b, P=0.929), or the probe trial (FIG. 18c, P=0.940). These results suggest that while these β-adrenergic receptor antagonists are effective in ameliorating memory deficits, they do not have detectable effects on "normal" subjects having no memory deficits.

Figure 15:
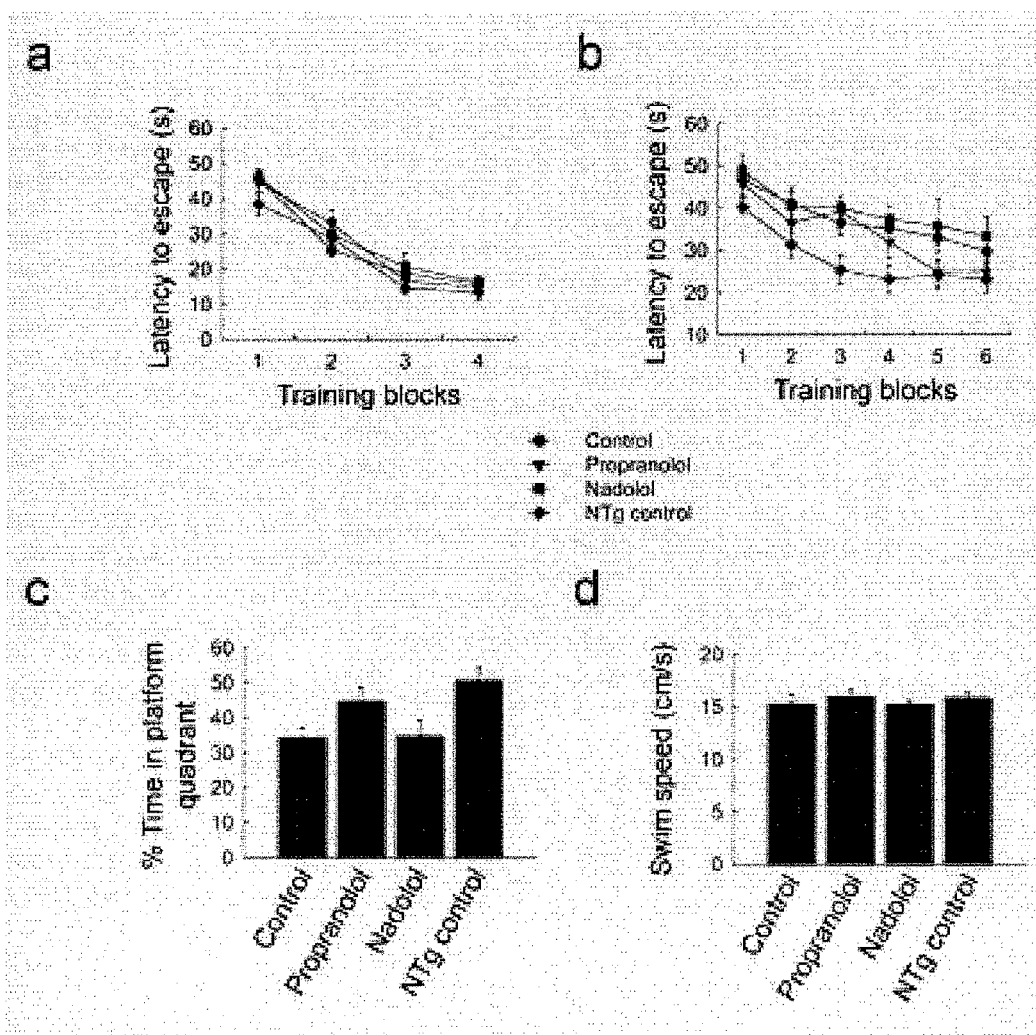
FIGS. 15a-15d show results from animal model studies. (a) Latencies to escape from visual platform training test. No genotype or drug effect was found on this training (F=2.145, P=0.096). (b) Latencies to escape in hidden platform training. The control mice showed significant impairment compared to non-transgenic mice (F=28.754, P<0.001), whereas propranolol treatment partially ameliorate the impairment comparing to control mice (F=4.571, P=0.034). Nadolol treatment showed no effect on the impairment (F=1.192, P=0.277). (c) Percent time spent in the platform quadrant in the probe trial. There was a significant genotype effect between control and non-transgenic control mice (P=0.002). Propranolol treatment partially ameliorated the impairment of spatial memory (P=0.048). Nadolol had no effect (P=0.969).
Figure 19:
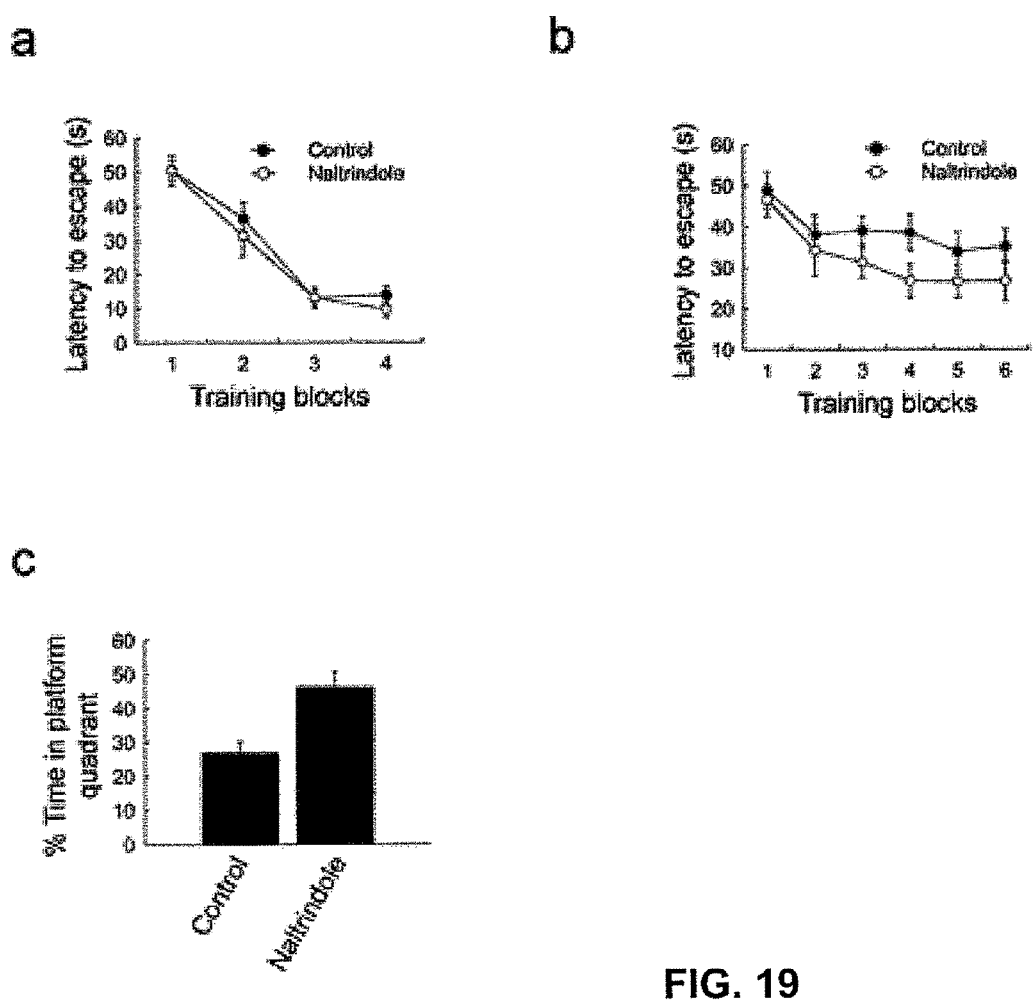
FIG. 19 shows results from tests similar to those in FIG. 15, but with DOR antagonist Naltrindole. Naltrindole is a DOR-selective antagonist that can cross the BBB. (a) In the visible platform training, no drug effect was observed (F=0.754, P=0.391). (b) In the hidden platform training, Naltrindole treatment ameliorated cognitive impairment (F=4.945, P<0.030). (c) In the probe trial, the effect of naltrindole was significant (P=0.006).

FIGS. 19A-19C show results from tests similar to those in FIG. 15, but with DOR antagonist Naltrindole. Naltrindole is a DOR-selective antagonist that can cross the BBB. FIG. 19a shows that in the visible platform training, no drug effect was observed (F=0.754, P=0.391), and FIG. 19b shows that in the hidden platform training, Naltrindole treatment ameliorated cognitive impairment (F 4.945, P<0.030). In the probe trial, the effect of naltrindole was significant (P=0.006), as shown in FIG. 19c.

Animal Model Experiment 2

In further animal experiments, four-month old APPswe/PS1ΔE9 double-transgenic mice were orally administered with saline (Sal), 2 mg/kg clenbuterol (Cle, a $\beta_2$AR-selective agonist) or 1 mg/kg ICI 118,551 (ICI, a $\beta_2$AR-selective antagonist) daily for 30 days. The mice were then tested with spatial learning and memory using a version of conventional Morris water maze substantially as described above.

The water maze was a circular 1.2 m pool filled with water at 24-25° C. and made opaque by the addition of milk powder. The pool was placed amid fixed spatial cues consisting of boldly patterned curtains and shelves containing distinct objects. Mice were gently lowered into the water facing the wall of the pool. Mice first underwent visible platform training for 2 consecutive days (eight trials per day), swimming to a raised circular platform (10 cm of diameter) marked with a pole. Visible platform days were split into two training blocks of four trials for statistical analysis. During visible platform training, both the platform location (NE, SE, SW, or NW) and start position (N, B, S, or W) were varied pseudo-randomly in each trial.

Figure 20:
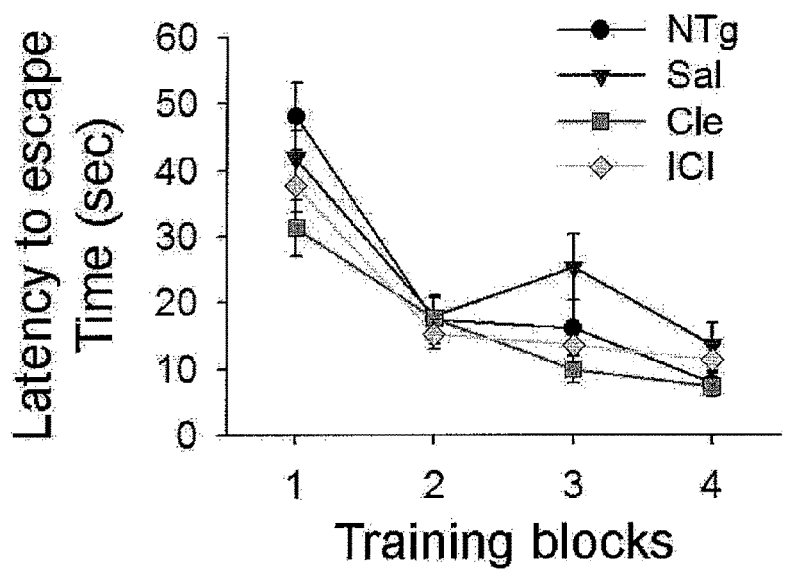
FIG. 20 shows escape latencies of saline (Sal), clenbuterol (Cle) and ICI 118,551 (ICI) treated double-transgenic mice together with the non-transgenic littermates (NTg) in the visible platform version of Morris water maze (2 blocks of 4 trials each day). No significant effect of drug treatments or transgene was found for either group of mice. (n=3-7).

As shown in FIG. 20, escape latencies of saline (Sal), clenbuterol (cle), and ICI 118,551 (ICI) treated double transgenic mice together with the non-transgenic littermates (NTg) in the visual platform version of Morris water maze exhibit small, but statistically insignificant, effects of drug treatments. Similarly, a small, but statistically insignificant, effect is seen between the Sal treated transgenic and non-transgenic mice. (n=3-7).

Hidden platform raining was conducted over 6 consecutive days (four trials per day), wherein mice were allowed to search for a platform submerged 1.5 cm beneath the surface of the water. Mice failing to reach the platform within 60 sec were led to the platform. During hidden-platform trials, the location of the platform remained constant, and mice entered the pool in one of the four pseudo-randomly selected locations (N, E, S, or W). After each hidden platform trial, mice remained on the platform for 30 sec and were removed from the platform and returned to their home cage.

Figure 21:
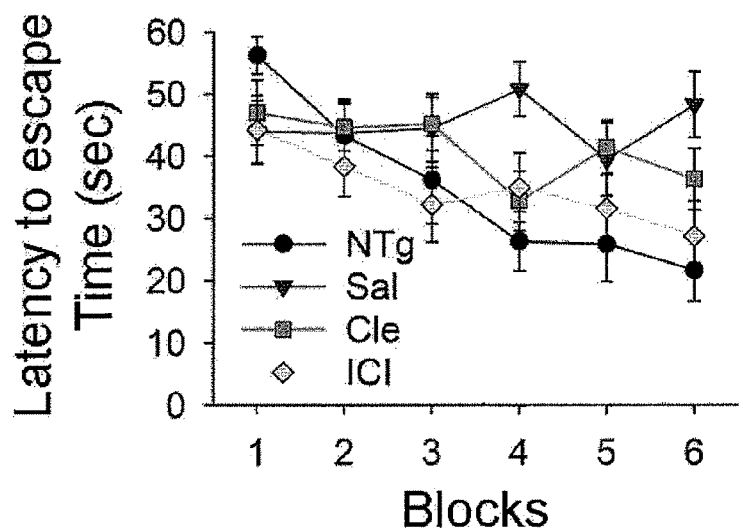
FIG. 21 shows escape latencies of saline (Sal), clenbuterol (Cle) and ICI 118,551 (ICI) treated double-transgenic mice together with the non-transgenic littermates (NTg) swimming to the hidden platform in the Morris water maze (1 blocks of 4 trials each day). A significant transgene effect was seen between NTg and Sal mice. The ICI mice displayed a faster learning curve than the Sal ones, whereas Cle treatment seemed to have no effect. (n=3-5).

FIG. 21 shows escape latencies of saline (Sal), clenbuterol (Cle) and ICI 118,551 (ICI) treated double-transgenic mice together with the non-transgenic littermates (NTg), swimming to a hidden platform in a Morris water maze (1 blocks of 4 trials each day). In this test, a significant transgenic effect was seen between NTg and Sal mice. The ICI mice displayed a faster learning curve than the Sal mice, whereas Cle treatment seemed to have no effect. (n=3-5). This results suggests that ICI treatment is quite effective in ameliorating the memory deficits of the transgenic mice.

Twenty-four hours after the final hidden platform training, a probe trial was conducted in which the platform was removed from the pool and mice were allowed to search for the platform for 60 sec. All trials were monitored by a camera mounted directly above the pool and were recorded and analyzed using a computerized tracking system.

Figure 22:
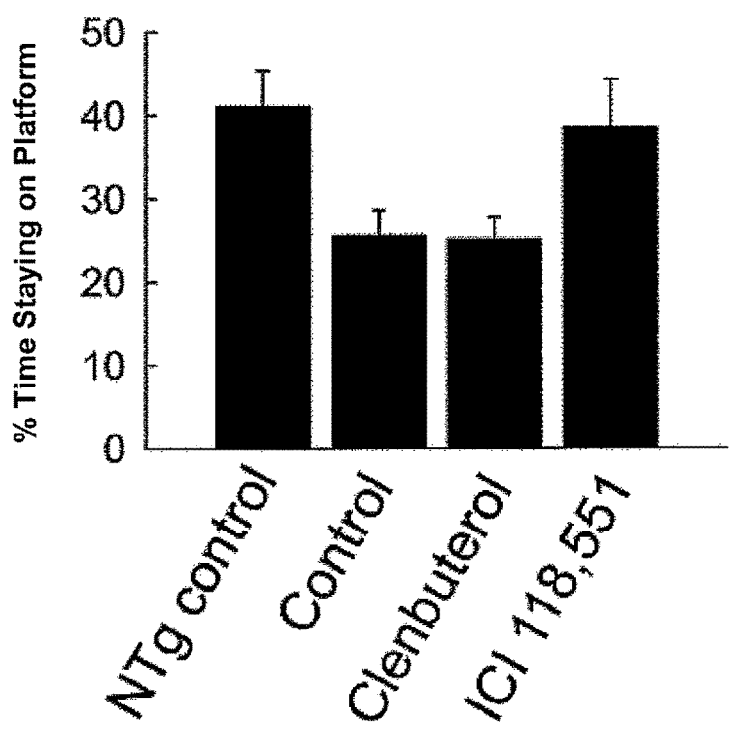
FIG. 22 shows percentage time spent on the platform during the probe trial run at 24-h after the final hidden platform training in the Morris water maze. The NTg and ICI mice spent greater proportion of time in the target quadrant. (n=3-5).

FIG. 22 shows percentage time spent on the platform during a probe trial run at 24-h after the final hidden platform training in a Morris water maze. The NTg and ICI mice spent greater proportion of time in the platform. (n=3-5), suggesting that ICI treatment conferred substantial effects in ameliorating the memory deficits.

Methods and Reagents

The following describes some specific procedures used in the experiments and examples discussed above. In the interest of clarity, general biochemical and molecular biology techniques used, which are well known to one skilled in the art, will not be described.

Reagents and Cell Transfection

All reagents were from Sigma or other commercial sources, unless otherwise indicated. Human FL-APP was cloned into pcDNA3 vector and mutated by PCR into the APPswe. The C99 with the signal peptide of APP was subcloned into pcDNA3 vector. The authenticity of the DNA sequences was confirmed by sequencing. The RNAi plasmid for human clathrin heavy chain was designed to target the sequence of 5'-GCTGGGAAAACTCTTCAGATT-3'. The NS RNAi was 5'-GGCCGCAAAGACCTTGTCCTTA-3'.

Animals and Drug Treatments

All animal experiments were conducted strictly in accordance with the National Institutes of Heath Guidelines for the Care and Use of Laboratory Animals. In acute experiments, Sprague-Dawly rats (from Shanghai SLAC Laboratory Animal Company) were injected intracerebroventricularly with 2 μg norepinephrine. The stereotaxic coordinates were: anterior-posterior, −0.9 mm; left-right, −1.5 mm; dorsal-ventral, −3.8 mm. Acute intraperitoneal injection of rats was performed with 0.5 mg/kg clenbuterol. In 30-d chronic experiments, APPswe/PS1ΔE9 mice (Jackson Laboratory) up to 5 months of age were instrumented with cannulae (anterior-posterior, 0.6 mm; left-right, 1.2 mm; dorsal-ventral, 1.8 mm) for daily injections of saline (n 4, two females and two males) and 3 nM isoproterenol (n=6, four females and two males). APPswe/PS1ΔE9 mice were daily subjected to oral administration of saline (n=6, three females and three males), 2 mg/kg per d clenbuterol (n=7, four females and three males), and 1 mg/kg per d ICI 118,551 (n=6, three females and three males).

Immunohistochemistry and Quantification of Amyloid Plaques

Mice were anesthetized and sacrificed by transcardiac saline perfusion. Brains were isolated, and the forebrain bisected midsagittally and was placed in 4% paraformaldehyde in phosphate buffer (pH 7.6) for 5 h at 4° C. Then, the post-fixed hemispheres were cryosectioned coronally into 10 μm sections. The sections were incubated with anti-Aβ 6E10 antibody (Chemicon), followed by TRITC-conjugated anti-mouse antibody incubation. The sections were then visualized and imaged using a laser confocal fluorescence microscope (Leica TCS Sβ2). Area of amyloid plaques was quantified with Image-Pro Plus 5.1 software (Media Cybernetic). Images were converted to gray scale by thresholding, and the area plaque was estimated.

Hippocampal Cultures and Acute Slices Preparation

Primary hippocampal cultures were prepared from 1-day-postnatal SD rats, electroporated using Amaxa Nucleofector system, maintained in B27/neurobasal medium (Invitrogen) for two weeks, and then used for agonist treatment. Acute hippocampal slices from 8-week-postnatal SD rats were prepared using a vibratome in ice-cold artificial CSF.

ELISA for Aβ

Cells were exposed to Iso (10 μM) or DADLE (1 μM) for 1 h and were further incubated in the conditioned medium for another 6 h. The conditioned medium was detected for $A\beta_{40}$ and $A\beta_{42}$ with sandwich ELISA kits (Biosource). Rat hippocampi were homogenized and centrifuged at 100,000×g for 1 h. Supernatants were detected for rat $A\beta_{40}$ and $A\beta_{42}$ with the BNT77/BA27 and BNT77/BC05 sandwich P-LISA kits (Wako) according to previous reports[52]. All measurements were performed in duplicate.

Immunoprecipitation

HEK293 cells or rat hippocampus slices were lysed in RIPA buffer. Flag-tagged receptors and endogenous DOR were immunoprecipitated with Flag antibody-conjugated beads or DOR antibody (Santa Cruz). The immunoprecipitated complexes were separated by SDS-PAGE and blotted with Flag, PS1-NTF, PS1-CTF, nicastrin, APH-1a and PEN-2 antibodies (Calbiochem). HEK293

Expressed Substrate Assay

The experiments were performed similarly as described previously[27]. HEK293 cells were lysed and aliquots (containing 50 μg proteins) were centrifuged at 13,000×g for 15 min. The cell membrane fractions were resuspended and then incubated at 37° C. for 2 h in 50 μl of assay buffer (pH 6.5) containing 1,10-phenanthroline, aprotinin, and leupeptin. The C60 generated from the incubated membrane fractions was measured by Western blot using HA antibody 12CA5.

Fluorogenic Substrate Assay

The assay was performed as reported[28,29]. Cells or hippocampal tissues were lysed or homogenized. Aliquots (containing 50 μg cell lysates or hippocampal homogenates) were centrifuged at 13,000×g for 15 min. The membrane pellets were resuspended and incubated at 37° C. for 2 h in 50 μl of assay buffer (pH 6.5) containing 12 μM fluorogenic substrates (Calbiochem). After incubation, fluorescence was measured using a spectrometer with excitation wavelength at 355 nm and emission wavelength at 440 nm.

Pulse-Chase Assay

HEK293 cells cotransfected with HA-C99 and DOR were starved for 2 h in methionine and serum free medium (Invitrogen) and subsequently pulse-labeled with 500 μCi [$^{35}$S] methionine (Amersham Pharmacia) in the absence or presence of DADLE for 1 h. The cells were then chased for 3 h in medium containing excess amounts of unlabeled methionine. The C99 in cell lysates was immunoprecipitated with 12CA5 and analyzed by autoradiography.

Immuno-Isolation of LEL

The experiments were modified from vesicle isolation protocol[53]. The homogenates from HEK293 cells cotransfected with $\beta_2$AR, C99 and Flag-Rab7 were centrifuged at 500×, g for 10 min. The resulting supernatants were incubated at 4° C. with M2 antibody-conjugated beads for 8 h. The isolated LEL were then subjected to Western blot with antibodies against LAMP-1 and EEA1 (BD Biosciences).

Immunofluorescence Microscopy

For experiments in HEK293 cells transfected with HA-tagged receptor together with or without GFP-Rab7 or GFP-Rab7 T22N, cells were fed with antibody 12CA5 for 30 min, treated with agonists, and then fixed. For the experiments in cells transfected with Flag-Rab7 and HA-Dyn K44A or GFP-Rab5 S34N, cells were treated with agonists and then fixed. For experiments in acute hippocampal slices, slices that exposed to Iso or DADLE were fixed and cryosectioned. The subsequent immuno-staining involved primary antibodies (including PS1-NTF, Flag, LAMP-1, or β-adaptin antibodies or FITC-conjugated HA antibody) and secondary antibodies (Cy3-conjugated anti-rabbit and FITC-conjugated anti-mouse antibodies, Jackson ImmunoResearch). Images were acquired using a laser confocal fluorescence microscope (Leica TCS Sβ2).

FRET Measurements of Receptor-PS1 Association

Images, with or without photo-bleaching, for FRET analysis were acquired with a Leica TCS SP2 confocal microscope and analyzed with software. Briefly, HEK293 cells were co-transfected with GFP-DOR and HA-ps1. HA-PS1 expression was detected by monitoring Cy3 fluorescence after incubation with a primary antibody against HA and a second antibody conjugated with Cy3 (Jackson ImmunoResearch), while GFP-DOR expression was identified by GFP fluorescence detection. Emission spectra from the cells expressing GFP-DOR or PS1-Cy3 were obtained with the X mode, using a 488 nm laser. For measurements of FRET efficiency by this method, Leica software application for acceptor photobleaching was applied. The selected cell surface areas were photobleached with a 561 nm laser, which bleached the Cy3 fluorophore. Reduction of the Cy3 signal after photo-bleaching in the GFP-DOR and HA-ps1 co-transfected HEK293 cells was 84±5.3% (n=50) on average. FRET was resolved as an increase in the GFP-DOR (donor) signal after photobleaching of ps1-Cy3 (acceptor). Relative FRET efficiency was calculated as (1-[Cy3 Ipre-bleach/Cy3 Ipost-bleach])×100%. For control purposes, an area of the cell surface without photo-bleaching was also analyzed for FRET.

Statistical Analysis

Data from cell experiments were analyzed by Student's t-test for comparison of independent means, with pooled estimates of common variances. The statistical significance of mouse data was determined by ANOVA followed by student's t-test.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for screening a reagent for treating Alzheimer's disease, comprising the following steps:
    (a) measuring a first extent of association between a receptor and presinilin-1 or γ-secretase, wherein the receptor is a G-protein coupled receptor that associates with presenilin-1;
    (b) measuring a second extent of association between the receptor and presinilin-1 or γ-secretase, under the same conditions as in step (a), in the presence of a candidate reagent;
    (c) determining a difference between the first extent of association and the second extent of association; and
    (d) repeating steps (a)-(c), with a different candidate agent if the difference is less than a threshold wherein the receptor is at least one selected from the group consisting of a β-adrenergic receptor and δ-opioid receptor.

2. The method in accordance with claim 1, wherein the β-adrenergic receptor is a type 2 β-adrenergic receptor (β2AR).

* * * * *